(12) United States Patent
Togami et al.

(10) Patent No.: US 8,183,434 B2
(45) Date of Patent: May 22, 2012

(54) METHOD FOR PRODUCING TRANSGENIC SURFACE LAYER CHIMERIC PLANT

(75) Inventors: Junichi Togami, Mishima-gun (JP); Ekaterina Mouradova, Mill Park (AU)

(73) Assignee: Suntory Holdings Limited, Osaka-shi, Osaka (JP)

( * ) Notice: Subject to any disclaimer, the term of this patent is extended or adjusted under 35 U.S.C. 154(b) by 364 days.

(21) Appl. No.: 12/532,522

(22) PCT Filed: Mar. 28, 2008

(86) PCT No.: PCT/JP2008/056746
§ 371 (c)(1),
(2), (4) Date: Sep. 22, 2009

(87) PCT Pub. No.: WO2008/120820
PCT Pub. Date: Oct. 9, 2008

(65) Prior Publication Data
US 2011/0088125 A1    Apr. 14, 2011

(30) Foreign Application Priority Data

Mar. 29, 2007  (JP) ................................ 2007-089259
Aug. 2, 2007   (JP) ................................ 2007-202291

(51) Int. Cl.
C12N 15/82  (2006.01)
C12N 15/84  (2006.01)
C12N 15/29  (2006.01)
C12N 15/54  (2006.01)
C12N 15/55  (2006.01)
A01H 5/00   (2006.01)

(52) U.S. Cl. ........ 800/282; 800/323; 800/294; 435/193; 435/195; 435/469; 536/23.6

(58) Field of Classification Search ......................... None
See application file for complete search history.

(56) References Cited

U.S. PATENT DOCUMENTS 5,480,789 A    1/1996  Firoozabady et al.
7,612,257 B2 * 11/2009  Brugliera et al. ............. 800/295

FOREIGN PATENT DOCUMENTS

| EP | 0 810 287 A1 | 12/1997 |
|----|---|---|
| JP | 10-501139 | 2/1998 |
| JP | 10-503374 | 3/1998 |
| JP | 11-505116 | 5/1999 |
| JP | 2001-190169 | 7/2001 |
| JP | 2002-315460 | 10/2002 |
| JP | 2003-523724 | 8/2003 |
| JP | 2006-512057 | 4/2006 |
| JP | 2006-280282 | 10/2006 |
| WO | 93/18155 | 9/1993 |
| WO | 96/04392 | 2/1996 |
| WO | 01/92536 | 12/2001 |
| WO | 2005/017147 | 2/2005 |

OTHER PUBLICATIONS

Finnegan et al. "Transgene Inactivation: Plants Fight Back!", Bio/Technology, vol. 12, Sep. 12, 1994, pp. 883-888.
Lazo et al., "A DNA Transformation-Competent *Arabidopsis* Genomic Library in *Agrobacterium*", Bio/Technology, vol. 9, Oct. 1991, pp. 963-967.
Fujiwara et al., "cDNA Cloning, Gene Expression and Subcellular Localization of Anthocyanin 5-aromatic Acyltransferase from *Gentiana triflora*", The Plant Journal, 1998, vol. 16, No. 4, pp. 421-431.
Mitsuhara et al., "Efficient Promoter Cassettes for Enhanced Expression of Foreign Genes in Dicotyledonous and Monocotyledonous Plants", Plant Cell Physiol., vol. 37, No. 1, 1996, pp. 49-59.
Kishimoto et al., "Random Primer o Riyo shita Kiku no Edakawari no Shuen Chimera Kozo no Kaiseki", Heisei 9 Nendo Yasai-Sagyo Kenkyu Seika Joho (1998), pp. 49 to 50. (English-language translation).
Kishimoto et al., "Kiku no Edakawari no Shuen Chimera Kozo no RAPD Bunseki", Norinsuisansho Yasai-Sagyo Shikenjo News (1997), vol. 49, p. 4. (English-language translation).
Tanaka et al., "Hana no Iro no Taisha Kogaku—Aoi Bara to Kankyo Mondai eno Torikumi-", Bio Industry, (2005), vol. 22, No. 8, pp. 33-38. (English-language translation).
International Search Report issued on May 13, 2008 in International PCT Application No. PCT/JP2008/056746 filed Mar. 28, 2008.
Kishimoto et al., "Random Primer o Riyo shita Kiku no Edakawari no Shuen Chimera Kozo no Kaiseki", Heisei 9 Nendo Yasai-Sagyo Kenkyu Seika Joho (1998), pp. 49 to 50. (Japanese-language only).
Kishimoto et al., "Kiku no Edakawari no Shuen Chimera Kozo no RAPD Bunseki", Norinsuisansho Yasai-Sagyo Shikenjo News (1997), vol. 49, p. 4. (Japanese-language only).
Tanaka et al., "Hana no Iro no Taisha Kogaku—Aoi Bara to Kankyo Mondai eno Torikumi-", BioIndustry, (2005), vol. 22, No. 8, pp. 33-38. (Japanese-language only).
Oono et al., "Effects of the Over-Expression of the *rolC* Gene on Leaf Development in Transgenic Periclinal Chimeric Plants", Plant Cell Physiol, (1993) vol. 34, No. 5, pp. 745-752.
Lambert et al., "Use of *Agrobacterium rhizogens* to Create Chimeric Apple Trees Through Genetic Grafting", Bio/Technology, (1991) vol. 9, pp. 80 and 83.
Li et al., "Observation of High-Frequency Occurrence of Chimeral Adventitious Shoots in Tissue Culture from the Chimeral Tissues of *Pelargonium zonale*", HortScience, (2005), vol. 40, No. 5, pp. 1461-1463.

(Continued)

Primary Examiner — David T Fox
(74) Attorney, Agent, or Firm — Drinker Biddle & Reath LLP

(57) ABSTRACT

A rose is produced in which an introduced gene is only present in a part of the cells thereof, such as cells of the L1 layer of flower petals, but is not present in germ cells such as pollen cells or ovule cells. Since the introduced gene is not propagated to other roses even when this rose is crossed with other roses, the possibility of dispersal of the introduced gene can be completely negated.

10 Claims, 3 Drawing Sheets

OTHER PUBLICATIONS

Extended European Search Report dated Jul. 7, 2010 from European Patent Application No. 08739852.5.

McCabe D. E. et al., "Transformation of elite cotton cultivars via particle bombardment of meristems", Bio/Technology, Nature Publishing Co., New York, US LNKD—DOI:10.1038/NBT0593-596, vol. 11, No. 5, May 1, 1993, pp. 596-598, XP002179156ISSN: 0733-222X.

Schmülling T. et al., "Transgenic tobacco plants regenerated from leaf disks can be periclinal chimeras", Plant Molecular Biology, Springer, Dordrecht, NL, vol. 21, No. 4, Feb. 1, 1993, pp. 705-708, XP009134798ISSN: 0167-4412.

Chandler Stephen et al., "Genetic modification in floriculture", Critical Reviews in Plant Sciences, vol. 26, No. 4, Jul. 2007, pp. 169-197, ISN: 0735-2689.

\* cited by examiner

Fig.2
WKS82
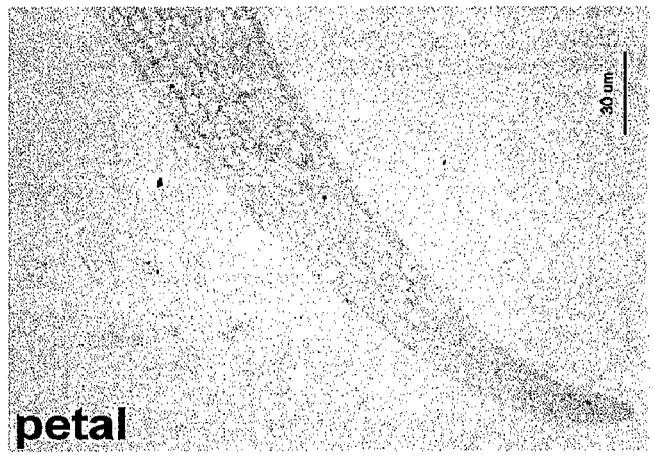
petal
WKS82/130-4-1
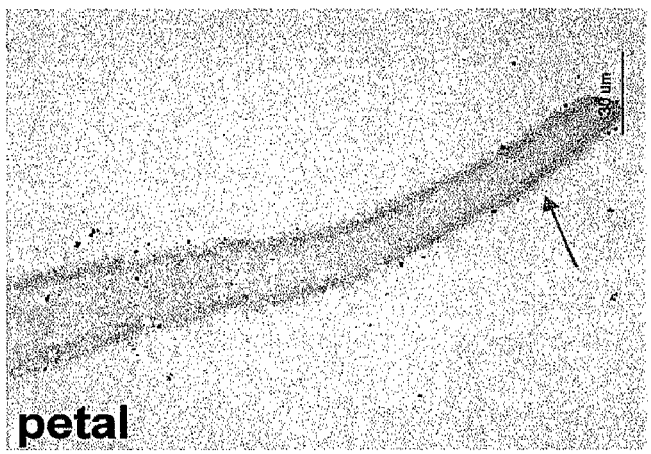
petal
WKS82/130-9-1
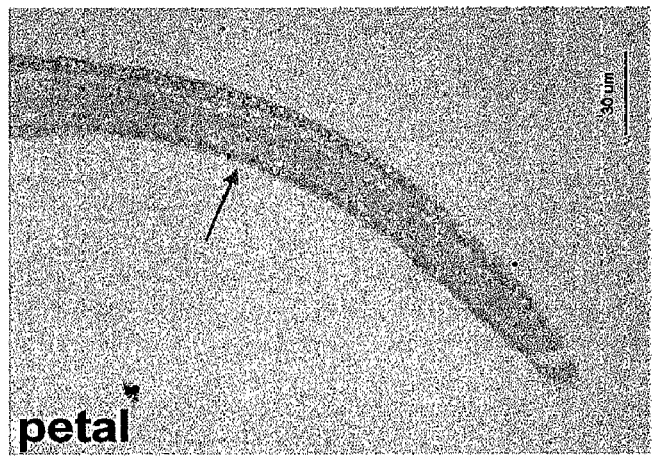
petal
(probe ; pansy F3'5'H)

SEQUENCE LISTING

```
<160> NUMBER OF SEQ ID NOS: 19

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (15)..(15)
<223> OTHER INFORMATION: Inosine

<400> SEQUENCE: 1
gayttyggnt ggggnaa                                                   17

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttttttttt tttttttctc gag                                            23

<210> SEQ ID NO 3
<211> LENGTH: 1808
```

```
<212> TYPE: DNA
<213> ORGANISM: Torenia sp.
<220> FEATURE:
<221> NAME/KEY: CDS
<222> LOCATION: (30)..(1466)

<400> SEQUENCE: 3
cttcaaagcc aaaaagaaac aattaatca atg gct gtt gaa gcc ccc aaa aca        53
                                 Met Ala Val Glu Ala Pro Lys Thr
                                  1               5 ata tgt gca gtc ctc gaa aac tct ctt att aca cca caa agt acc gat       101
Ile Cys Ala Val Leu Glu Asn Ser Leu Ile Thr Pro Gln Ser Thr Asp
 10                  15                  20 aca gaa caa act ctt tca ctc aca ttc ttt gac atc aaa tgg gtt cat       149
Thr Glu Gln Thr Leu Ser Leu Thr Phe Phe Asp Ile Lys Trp Val His
 25                  30                  35                  40 ttt cat cca atg caa tgc ctt gtg ttg tac aac ttc cca tgt tct aag       197
Phe His Pro Met Gln Cys Leu Val Leu Tyr Asn Phe Pro Cys Ser Lys
                 45                  50                  55 tca cat ttt ctc gaa gcc aca gtt ccg agc ttc aaa tca tca ctc tcc       245
Ser His Phe Leu Glu Ala Thr Val Pro Ser Phe Lys Ser Ser Leu Ser
             60                  65                  70 aaa act ctc aga cac tat ctt cca tta tca gga aac tta tac tat cca       293
Lys Thr Leu Arg His Tyr Leu Pro Leu Ser Gly Asn Leu Tyr Tyr Pro
         75                  80                  85 aac ccg acc cat gac atg gat gat gat gaa tcg aac atg ccc gag atc       341
Asn Pro Thr His Asp Met Asp Asp Asp Glu Ser Asn Met Pro Glu Ile
     90                  95                 100 cgt tat aaa cct ggc gac tcg gtt tct cta acc gtt gca gag tac ttc       389
Arg Tyr Lys Pro Gly Asp Ser Val Ser Leu Thr Val Ala Glu Tyr Phe
105                 110                 115                 120 tcc ggt cat gaa gac aat acg act act gaa gaa tac ttc aat tac ctc       437
Ser Gly His Glu Asp Asn Thr Thr Thr Glu Glu Tyr Phe Asn Tyr Leu
                125                 130                 135 act gga aat ttc cag aga gat tgc gat caa ttc tat gat ctc tta ccc       485
Thr Gly Asn Phe Gln Arg Asp Cys Asp Gln Phe Tyr Asp Leu Leu Pro
            140                 145                 150 gat ttt cga gac ccg gaa acc gaa tcc aat tgc aca gta atc cca ctt       533
Asp Phe Arg Asp Pro Glu Thr Glu Ser Asn Cys Thr Val Ile Pro Leu
        155                 160                 165 ata gca gtt caa atc aca ctc ttt cca ggt gct ggg ata tgt ctg ggg       581
Ile Ala Val Gln Ile Thr Leu Phe Pro Gly Ala Gly Ile Cys Leu Gly
    170                 175                 180 gtc atc aac agt cac gta gtt ggc gat gcg agt tcc ata gtg gga ttc       629
Val Ile Asn Ser His Val Val Gly Asp Ala Ser Ser Ile Val Gly Phe
185                 190                 195                 200 atc aaa gct tgg agt aaa gtt gca atg tat gaa gac gat gaa gag att       677
Ile Lys Ala Trp Ser Lys Val Ala Met Tyr Glu Asp Asp Glu Glu Ile
                205                 210                 215 cta gct aac aac aat ttg att cca tct tat gac aga tca gtg gtg aaa       725
Leu Ala Asn Asn Asn Leu Ile Pro Ser Tyr Asp Arg Ser Val Val Lys
            220                 225                 230 gat cca aaa ggg atc aaa tct ttg ctc tgg aac aag atg aag aac gtg       773
Asp Pro Lys Gly Ile Lys Ser Leu Leu Trp Asn Lys Met Lys Asn Val
        235                 240                 245 aaa tat caa ccc caa ccc gca aaa cat ctc cca aca aac aag gtc cga       821
Lys Tyr Gln Pro Gln Pro Ala Lys His Leu Pro Thr Asn Lys Val Arg
    250                 255                 260 gcc aca tac acc ttg aga aag aac gat atc gag agg ctg aaa acc cga       869
Ala Thr Tyr Thr Leu Arg Lys Asn Asp Ile Glu Arg Leu Lys Thr Arg
265                 270                 275                 280
```

```
atc cga tcc aag aaa cca ggc aca acc tgc tta tca tct ttc aca atc      917
Ile Arg Ser Lys Lys Pro Gly Thr Thr Cys Leu Ser Ser Phe Thr Ile
            285                 290                 295 gca aca gcc tat gct tgg aca tgc ctt gca aaa tct gca gca gaa gct      965
Ala Thr Ala Tyr Ala Trp Thr Cys Leu Ala Lys Ser Ala Ala Glu Ala
        300                 305                 310 gaa gaa caa gta gtc caa gac agt gac gac gag cac ttg ctc atg ccc     1013
Glu Glu Gln Val Val Gln Asp Ser Asp Asp Glu His Leu Leu Met Pro
    315                 320                 325 gtt gat ttg aga cca aga ata gat cct cca tta cca cct tct tac ttt     1061
Val Asp Leu Arg Pro Arg Ile Asp Pro Pro Leu Pro Pro Ser Tyr Phe
330                 335                 340 gga aac tgc gtt ctt cca tct ttt gcg aaa acg acg cat ggg ctt ttg     1109
Gly Asn Cys Val Leu Pro Ser Phe Ala Lys Thr Thr His Gly Leu Leu
345                 350                 355                 360 aaa gga gag tta ggg ctt ttt aat gca gtg gaa gtg att agt gat gtc     1157
Lys Gly Glu Leu Gly Leu Phe Asn Ala Val Glu Val Ile Ser Asp Val
            365                 370                 375 att acc ggt atc gtt agc aag aaa tat gac ttg ttc aaa gac tta gac     1205
Ile Thr Gly Ile Val Ser Lys Lys Tyr Asp Leu Phe Lys Asp Leu Asp
        380                 385                 390 aga caa ggt gag att ttt cgt gcc ttg ttc gga aaa cga gtg ttg gcg     1253
Arg Gln Gly Glu Ile Phe Arg Ala Leu Phe Gly Lys Arg Val Leu Ala
    395                 400                 405 atc atg ggt tcg cct aag ttc gat ctc tac gaa gtt gat ttc ggg tgg     1301
Ile Met Gly Ser Pro Lys Phe Asp Leu Tyr Glu Val Asp Phe Gly Trp
410                 415                 420 ggt aag ccg aag aag att gaa cct gtg tcc att gat aga gag agg acg     1349
Gly Lys Pro Lys Lys Ile Glu Pro Val Ser Ile Asp Arg Glu Arg Thr
425                 430                 435                 440 act atg tgg att agc aag tct ggc gag ttt gag ggt gga ttg gag att     1397
Thr Met Trp Ile Ser Lys Ser Gly Glu Phe Glu Gly Gly Leu Glu Ile
            445                 450                 455 ggt ttt tct ttc aat aag aag aaa atg gat gct ttt ggc gag tgt ttt     1445
Gly Phe Ser Phe Asn Lys Lys Lys Met Asp Ala Phe Gly Glu Cys Phe
        460                 465                 470 aac agc ggt ttg aag gat att taatttaaaa aattgtttag ctttgatgca        1496
Asn Ser Gly Leu Lys Asp Ile
    475 tgcgttttat atatgttgtg aaataatgtg gtgtgcaata actagagtaa ctttaggtta   1556 ataaattcgg tttttctgtt aaatctggat gattcgtgca agcaaactgt cgatgcgttg   1616 gatggatgtc gggtggtgtg gagattgttg aagaaggaaa tggatgcttt ttttatggtg   1676 gtttgaagga tttgaatgtg tagattattg gtttattgag gttgtttata tttgtgtatg   1736 ttgtttatgc atgaaaaata tttagatccc aacattttat gtatgacgtg gtttaatatt   1796 tcgatttcga tc                                                       1808

<210> SEQ ID NO 4
<211> LENGTH: 1781
<212> TYPE: DNA
<213> ORGANISM: Viola tricolor
<220> FEATURE:
<221> NAME/KEY: CDS
<222> LOCATION: (7)..(1524)

<400> SEQUENCE: 4 gacaac atg gca att cta gtc acc gac ttc gtt gtc gcg gct ata att       48
       Met Ala Ile Leu Val Thr Asp Phe Val Val Ala Ala Ile Ile
        1               5                   10 ttc ttg atc act cgg ttc tta gtt cgt tct ctt ttc aag aaa cca acc      96
```

```
                -continued

Phe Leu Ile Thr Arg Phe Leu Val Arg Ser Leu Phe Lys Lys Pro Thr
 15              20                  25                  30 cga ccg ctc ccc cgg ggt cct ctc ggt tgg ccc ttg gtg ggc gcc ctc    144
Arg Pro Leu Pro Pro Gly Pro Leu Gly Trp Pro Leu Val Gly Ala Leu
                 35                  40                  45 cct ctc cta ggc gcc atg cct cac gtc gca cta gcc aaa ctc gct aag    192
Pro Leu Leu Gly Ala Met Pro His Val Ala Leu Ala Lys Leu Ala Lys
             50                  55                  60 aag tat ggt ccg atc atg cac cta aaa atg ggc acg tgc gac atg gtg    240
Lys Tyr Gly Pro Ile Met His Leu Lys Met Gly Thr Cys Asp Met Val
         65                  70                  75 gtc gcg tcc acc ccc gag tcg gct cga gcc ttc ctc aaa acg cta gac    288
Val Ala Ser Thr Pro Glu Ser Ala Arg Ala Phe Leu Lys Thr Leu Asp
     80                  85                  90 ctc aac ttc tcc aac cgc cca ccc aac gcg ggc gca tcc cac cta gcg    336
Leu Asn Phe Ser Asn Arg Pro Pro Asn Ala Gly Ala Ser His Leu Ala
 95                 100                 105                 110 tac ggc gcg cag gac tta gtc ttc gcc aag tac ggt ccg agg tgg aag    384
Tyr Gly Ala Gln Asp Leu Val Phe Ala Lys Tyr Gly Pro Arg Trp Lys
                115                 120                 125 act tta aga aaa ttg agc aac ctc cac atg cta ggc ggg aag gcg ttg    432
Thr Leu Arg Lys Leu Ser Asn Leu His Met Leu Gly Gly Lys Ala Leu
            130                 135                 140 gat gat tgg gca aat gtg agg gtc acc gag cta ggc cac atg ctt aaa    480
Asp Asp Trp Ala Asn Val Arg Val Thr Glu Leu Gly His Met Leu Lys
            145                 150                 155 gcc atg tgc gag gcg agc cgg tgc ggg gag ccc gtg gtg ctg gcc gag    528
Ala Met Cys Glu Ala Ser Arg Cys Gly Glu Pro Val Val Leu Ala Glu
        160                 165                 170 atg ctc acg tac gcc atg gcg aac atg atc ggt caa gtg ata ctc agc    576
Met Leu Thr Tyr Ala Met Ala Asn Met Ile Gly Gln Val Ile Leu Ser
175                 180                 185                 190 cgg cgc gtg ttc gtg acc aaa ggg acc gag tct aac gag ttc aaa gac    624
Arg Arg Val Phe Val Thr Lys Gly Thr Glu Ser Asn Glu Phe Lys Asp
                195                 200                 205 atg gtg gtc gag ttg atg acg tcc gcc ggg tac ttc aac atc ggt gac    672
Met Val Val Glu Leu Met Thr Ser Ala Gly Tyr Phe Asn Ile Gly Asp
            210                 215                 220 ttc ata ccc tcg atc gct tgg atg gat ttg caa ggg atc gag cga ggg    720
Phe Ile Pro Ser Ile Ala Trp Met Asp Leu Gln Gly Ile Glu Arg Gly
            225                 230                 235 atg aag aag ctg cac acg aag ttt gat gtg tta ttg acg aag atg gtg    768
Met Lys Lys Leu His Thr Lys Phe Asp Val Leu Leu Thr Lys Met Val
        240                 245                 250 aag gag cat aga gcg acg agt cat gag cgc aaa ggg aag gca gat ttc    816
Lys Glu His Arg Ala Thr Ser His Glu Arg Lys Gly Lys Ala Asp Phe
255                 260                 265                 270 ctc gac gtt ctc ttg gaa gaa tgc gac aat aca aat ggg gag aag ctt    864
Leu Asp Val Leu Leu Glu Glu Cys Asp Asn Thr Asn Gly Glu Lys Leu
                275                 280                 285 agt att acc aat atc aaa gct gtc ctt ttg aat cta ttc acg gcg ggc    912
Ser Ile Thr Asn Ile Lys Ala Val Leu Leu Asn Leu Phe Thr Ala Gly
            290                 295                 300 acg gac aca tct tcg agc ata atc gaa tgg gcg tta acg gag atg atc    960
Thr Asp Thr Ser Ser Ser Ile Ile Glu Trp Ala Leu Thr Glu Met Ile
            305                 310                 315 aag aat ccg acg atc tta aaa aag gcg caa gag gag atg gat cga gtc   1008
Lys Asn Pro Thr Ile Leu Lys Lys Ala Gln Glu Glu Met Asp Arg Val
        320                 325                 330 atc ggt cgt gat cgg agg ctg ctc gaa tcg gac ata tcg agc ctc ccg   1056
```

```
Ile Gly Arg Asp Arg Arg Leu Leu Glu Ser Asp Ile Ser Ser Leu Pro
335                 340                 345                 350 tac cta caa gcc att gct aaa gaa acg tat cgc aaa cac ccg tcg acg    1104
Tyr Leu Gln Ala Ile Ala Lys Glu Thr Tyr Arg Lys His Pro Ser Thr
                355                 360                 365 cct ctc aac ttg ccg agg att gcg atc caa gca tgt gaa gtt gat ggc    1152
Pro Leu Asn Leu Pro Arg Ile Ala Ile Gln Ala Cys Glu Val Asp Gly
            370                 375                 380 tac tac atc cct aag gac gcg agg ctt agc gtg aac att tgg gcg atc    1200
Tyr Tyr Ile Pro Lys Asp Ala Arg Leu Ser Val Asn Ile Trp Ala Ile
        385                 390                 395 ggt cgg gac ccg aat gtt tgg gag aat ccg ttg gag ttc ttg ccg gaa    1248
Gly Arg Asp Pro Asn Val Trp Glu Asn Pro Leu Glu Phe Leu Pro Glu
    400                 405                 410 aga ttc ttg tct gaa gag aat ggg aag atc aat ccc ggt ggg aat gat    1296
Arg Phe Leu Ser Glu Glu Asn Gly Lys Ile Asn Pro Gly Gly Asn Asp
415                 420                 425                 430 ttt gag ctg att ccg ttt gga gcc ggg agg aga att tgt gcg ggg aca    1344
Phe Glu Leu Ile Pro Phe Gly Ala Gly Arg Arg Ile Cys Ala Gly Thr
                435                 440                 445 agg atg gga atg gtc ctt gta agt tat att ttg ggc act ttg gtc cat    1392
Arg Met Gly Met Val Leu Val Ser Tyr Ile Leu Gly Thr Leu Val His
                450                 455                 460 tct ttt gat tgg aaa tta cca aat ggt gtc gct gag ctt aat atg gat    1440
Ser Phe Asp Trp Lys Leu Pro Asn Gly Val Ala Glu Leu Asn Met Asp
            465                 470                 475 gaa agt ttt ggg ctt gca ttg caa aag gcc gtg ccg ctc tcg gcc ttg    1488
Glu Ser Phe Gly Leu Ala Leu Gln Lys Ala Val Pro Leu Ser Ala Leu
        480                 485                 490 gtc agc cca cgg ttg gcc tca aac gcg tac gca acc tgagctaatg         1534
Val Ser Pro Arg Leu Ala Ser Asn Ala Tyr Ala Thr
495                 500                 505 ggctgggcct agttttgtgg gccttaattt agagactttt gtgttttaag gtgtgtactt   1594
tattaattgg gtgcttaaat gtgtgtttta atttgtattt atggttaatt atgactttat   1654
tgtataatta tttatttttc ccttctgggt atttttatcca tttaattttt cttcagaatt   1714
atgatcatag ttatcagaat aaaattgaaa ataatgaatc ggaaaaaaaa aaaaaaaaaa   1774
aaaaaaa                                                            1781

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagctaggcc acatgctta                                                 19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctttgcgctc atgactcgt                                                 19
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aacaatatgt gcagtcctcg aa                                            22

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aactcgcatc gccaactac                                                19

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gattgaacaa gatggattgc acgc                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgaagaactc cagcatgaga tccc                                          24

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttgatcttc ccattgagc                                                19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccgcggtgg gaagatcccc                                               20

<210> SEQ ID NO 13
<211> LENGTH: 6

-continued

```
<212> TYPE: PRT
<213> ORGANISM: Torenia sp.

<400> SEQUENCE: 13

Asp Phe Gly Trp Gly Lys
1               5

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atttccgcct cattagaagg                                                 20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcctcatgtt tccatttgtc g                                               21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atggaggctc gtccagttca t                                               21

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcaattatcg attttgggac gc                                              22

<210> SEQ ID NO 18
<211> LENGTH: 479
<212> TYPE: PRT
<213> ORGANISM: Torenia sp.

<400> SEQUENCE: 18

Met Ala Val Glu Ala Pro Lys Thr Ile Cys Ala Val Leu Glu Asn Ser
1               5                   10                  15

Leu Ile Thr Pro Gln Ser Thr Asp Thr Glu Gln Thr Leu Ser Leu Thr
                20                  25                  30

Phe Phe Asp Ile Lys Trp Val His Phe His Pro Met Gln Cys Leu Val
            35                  40                  45

Leu Tyr Asn Phe Pro Cys Ser Lys Ser His Phe Leu Glu Ala Thr Val
        50                  55                  60
```

```
Pro Ser Phe Lys Ser Ser Leu Ser Lys Thr Leu Arg His Tyr Leu Pro
65                  70                  75                  80

Leu Ser Gly Asn Leu Tyr Tyr Pro Asn Pro Thr His Asp Met Asp Asp
                85                  90                  95

Asp Glu Ser Asn Met Pro Glu Ile Arg Tyr Lys Pro Gly Asp Ser Val
            100                 105                 110

Ser Leu Thr Val Ala Glu Tyr Phe Ser Gly His Glu Asp Asn Thr Thr
        115                 120                 125

Thr Glu Glu Tyr Phe Asn Tyr Leu Thr Gly Asn Phe Gln Arg Asp Cys
    130                 135                 140

Asp Gln Phe Tyr Asp Leu Leu Pro Asp Phe Arg Asp Pro Glu Thr Glu
145                 150                 155                 160

Ser Asn Cys Thr Val Ile Pro Leu Ile Ala Val Gln Ile Thr Leu Phe
                165                 170                 175

Pro Gly Ala Gly Ile Cys Leu Gly Val Ile Asn Ser His Val Val Gly
            180                 185                 190

Asp Ala Ser Ser Ile Val Gly Phe Ile Lys Ala Trp Ser Lys Val Ala
        195                 200                 205

Met Tyr Glu Asp Asp Glu Glu Ile Leu Ala Asn Asn Leu Ile Pro
210                 215                 220

Ser Tyr Asp Arg Ser Val Val Lys Asp Pro Lys Gly Ile Lys Ser Leu
225                 230                 235                 240

Leu Trp Asn Lys Met Lys Asn Val Lys Tyr Gln Pro Gln Pro Ala Lys
                245                 250                 255

His Leu Pro Thr Asn Lys Val Arg Ala Thr Tyr Thr Leu Arg Lys Asn
                260                 265                 270

Asp Ile Glu Arg Leu Lys Thr Arg Ile Arg Ser Lys Lys Pro Gly Thr
            275                 280                 285

Thr Cys Leu Ser Ser Phe Thr Ile Ala Thr Ala Tyr Ala Trp Thr Cys
        290                 295                 300

Leu Ala Lys Ser Ala Ala Glu Ala Glu Glu Gln Val Val Gln Asp Ser
305                 310                 315                 320

Asp Asp Glu His Leu Leu Met Pro Val Asp Leu Arg Pro Arg Ile Asp
                325                 330                 335

Pro Pro Leu Pro Pro Ser Tyr Phe Gly Asn Cys Val Leu Pro Ser Phe
            340                 345                 350

Ala Lys Thr Thr His Gly Leu Leu Lys Gly Glu Leu Gly Leu Phe Asn
        355                 360                 365

Ala Val Glu Val Ile Ser Asp Val Ile Thr Gly Ile Val Ser Lys Lys
    370                 375                 380

Tyr Asp Leu Phe Lys Asp Leu Asp Arg Gln Gly Glu Ile Phe Arg Ala
385                 390                 395                 400

Leu Phe Gly Lys Arg Val Leu Ala Ile Met Gly Ser Pro Lys Phe Asp
                405                 410                 415

Leu Tyr Glu Val Asp Phe Gly Trp Gly Lys Pro Lys Lys Ile Glu Pro
                420                 425                 430

Val Ser Ile Asp Arg Glu Arg Thr Thr Met Trp Ile Ser Lys Ser Gly
            435                 440                 445

Glu Phe Glu Gly Gly Leu Glu Ile Gly Phe Ser Phe Asn Lys Lys Lys
        450                 455                 460

Met Asp Ala Phe Gly Glu Cys Phe Asn Ser Gly Leu Lys Asp Ile
465                 470                 475
```

<210> SEQ ID NO 19

-continued

```
<211> LENGTH: 506
<212> TYPE: PRT
<213> ORGANISM: Viola tricolor

<400> SEQUENCE: 19

Met Ala Ile Leu Val Thr Asp Phe Val Ala Ala Ile Ile Phe Leu
1               5                   10                  15

Ile Thr Arg Phe Leu Val Arg Ser Leu Phe Lys Lys Pro Thr Arg Pro
            20                  25                  30

Leu Pro Pro Gly Pro Leu Gly Trp Pro Leu Val Gly Ala Leu Pro Leu
                35                  40                  45

Leu Gly Ala Met Pro His Val Ala Leu Ala Lys Leu Ala Lys Lys Tyr
50                  55                  60

Gly Pro Ile Met His Leu Lys Met Gly Thr Cys Asp Met Val Val Ala
65                  70                  75                  80

Ser Thr Pro Glu Ser Ala Arg Ala Phe Leu Lys Thr Leu Asp Leu Asn
                85                  90                  95

Phe Ser Asn Arg Pro Pro Asn Ala Gly Ala Ser His Leu Ala Tyr Gly
            100                 105                 110

Ala Gln Asp Leu Val Phe Ala Lys Tyr Gly Pro Arg Trp Lys Thr Leu
        115                 120                 125

Arg Lys Leu Ser Asn Leu His Met Leu Gly Gly Lys Ala Leu Asp Asp
    130                 135                 140

Trp Ala Asn Val Arg Val Thr Glu Leu Gly His Met Leu Lys Ala Met
145                 150                 155                 160

Cys Glu Ala Ser Arg Cys Gly Glu Pro Val Val Leu Ala Glu Met Leu
                165                 170                 175

Thr Tyr Ala Met Ala Asn Met Ile Gly Gln Val Ile Leu Ser Arg Arg
            180                 185                 190

Val Phe Val Thr Lys Gly Thr Glu Ser Asn Glu Phe Lys Asp Met Val
        195                 200                 205

Val Glu Leu Met Thr Ser Ala Gly Tyr Phe Asn Ile Gly Asp Phe Ile
    210                 215                 220

Pro Ser Ile Ala Trp Met Asp Leu Gln Gly Ile Glu Arg Gly Met Lys
225                 230                 235                 240

Lys Leu His Thr Lys Phe Asp Val Leu Leu Thr Lys Met Val Lys Glu
                245                 250                 255

His Arg Ala Thr Ser His Glu Arg Lys Gly Lys Ala Asp Phe Leu Asp
            260                 265                 270

Val Leu Leu Glu Glu Cys Asp Asn Thr Asn Gly Glu Lys Leu Ser Ile
        275                 280                 285

Thr Asn Ile Lys Ala Val Leu Leu Asn Leu Phe Thr Ala Gly Thr Asp
    290                 295                 300

Thr Ser Ser Ser Ile Ile Glu Trp Ala Leu Thr Glu Met Ile Lys Asn
305                 310                 315                 320

Pro Thr Ile Leu Lys Lys Ala Gln Glu Glu Met Asp Arg Val Ile Gly
                325                 330                 335

Arg Asp Arg Arg Leu Leu Glu Ser Asp Ile Ser Ser Leu Pro Tyr Leu
            340                 345                 350

Gln Ala Ile Ala Lys Glu Thr Tyr Arg Lys His Pro Ser Thr Pro Leu
        355                 360                 365

Asn Leu Pro Arg Ile Ala Ile Gln Ala Cys Glu Val Asp Gly Tyr Tyr
    370                 375                 380

Ile Pro Lys Asp Ala Arg Leu Ser Val Asn Ile Trp Ala Ile Gly Arg
385                 390                 395                 400
```

```
Asp Pro Asn Val Trp Glu Asn Pro Leu Glu Phe Leu Pro Glu Arg Phe
            405                 410                415

Leu Ser Glu Glu Asn Gly Lys Ile Asn Pro Gly Gly Asn Asp Phe Glu
            420                 425                430

Leu Ile Pro Phe Gly Ala Gly Arg Arg Ile Cys Ala Gly Thr Arg Met
            435                 440                445

Gly Met Val Leu Val Ser Tyr Ile Leu Gly Thr Leu Val His Ser Phe
        450             455                 460

Asp Trp Lys Leu Pro Asn Gly Val Ala Glu Leu Asn Met Asp Glu Ser
465                 470                 475                 480

Phe Gly Leu Ala Leu Gln Lys Ala Val Pro Leu Ser Ala Leu Val Ser
                485                 490                 495

Pro Arg Leu Ala Ser Asn Ala Tyr Ala Thr
            500                 505
```

METHOD FOR PRODUCING TRANSGENIC SURFACE LAYER CHIMERIC PLANT

CROSS REFERENCE TO RELATED APPLICATIONS

This application is the National Stage of International Application No. PCT/JP2008/056746 filed Mar. 28, 2008, and claims benefit of Japanese Patent Application Nos. 2007-089259 filed Mar. 29, 2007 and 2007-202291 filed Aug. 2, 2007, which are herein incorporated by reference in their entirety.

REFERENCE TO A SEQUENCE LISTING

A Sequence Listing containing SEQ ID NOS: 1-12 is incorporated herein by reference.

TECHNICAL FIELD

The present invention provides a method for producing a chimeric transgenic plant having an introduced gene in a part of the cells thereof.

BACKGROUND ART

Individuals composed of a plurality of genetically different cell groups are referred to as chimeras. Plant chimeras are classified as periclinal chimeras, partial chimeras and sectorial chimeras according to their structure, and can be produced by, for example, grafting as well as accidental or radiation-induced somatic mutations or chromosome doubling induced by chemical treatment.

Sectorial chimeras are non-structural chimeras derived from the layered structure of plants, and occur due to proliferation of mutant cells present non-structurally at growth points. Namely, sectorial chimeras refer to chimeras in which a single tissue layer itself is chimeric, and frequently appear in the form of different colored stripes in flowers, leaves, stems and other organs. Although sectorial chimeras usually disappear due to their instability, periclinal chimeras occasionally continue to develop.

Periclinal chimeras refer to structural chimeras derived from the tissue layer structure of plants in which sectorial chimeras develop and a single cell layer is completely substituted with mutant cells. In the case of periclinal chimeras, a single tissue layer itself is homogeneous and not chimeric. Periclinal chimeras are stable and the frequency at which they disappear is said to be low. Plant cell tissue is basically composed of three cell layers, having a tissue layer structure consisting of a first layer (L1), a second layer (L2) and a third layer (L3) moving inward from the outside.

The L1 and L2 layers arise from the two layers of tunica of growth points, while the L3 layer arises from the corpus. In nearly all plant species, the epidermis is entirely formed from the L1 layer, while the L2 layer is involved with the germ cell system. Although numerous periclinal chimeras having different properties for each of these cell layers are horticulturally important and have high industrial value, the probability of obtaining a periclinal chimera accidentally or by a means in which mutations are induced artificially in the manner of radiation exposure or chemical treatment is extremely low.

When introducing a foreign gene into a plant body, it is not easy to artificially produce a chimeric plant having an introduced gene in only a part of the cells. Previously, there is an example of the production of a chimeric plant having an introduced gene in only a part of germ cells or the L2 cell layer by introducing a gene into an immature corn embryo by a method using a particle gun (Japanese Unexamined International Publication No. H10-503374). However, in the case of introducing a gene mediated by *Agrobacterium*, it is even more difficult to produce a chimeric plant. In methods of *Agrobacterium*-mediated gene introduction, single cells in which the gene has been introduced are selected by using as an indicator a trait such as drug resistance as determined through expression of a marker gene, and a single individual transgenic plant is obtained from the single cell in which the gene has been introduced.

Accordingly, normally obtained transgenic plants are composed of genetically a single kind of cell, and all of the cells have the introduced gene. Even if a plant that only had a foreign gene in a part of the cells (chimeric plant) was obtained, it would merely constitute an accidental result, and it is extremely difficult to control gene introduction so that the gene is only introduced into cells of a specific portion of a plant with the current level of technology. In addition, even if such a plant were obtained accidentally, the probability of the plant being a periclinal chimera having the gene only in a part of the cell layers is considered to be extremely low as previously described.

During the course of selecting cells having an introduced gene, although chimeric cell clusters or chimeric plant bodies may appear in which a foreign gene has been introduced into only a part thereof, in this case, the chimeric cell cluster or plant body is either chimeric throughout all cell layers or only a single tissue layer itself is chimeric, and is not a true periclinal chimera (that in which a foreign gene is introduced in only a specific cell layer while the cell layer itself is homogeneous). There have previously been very few examples of the production of a truly periclinal chimeric transgenic plant that has been verified by molecular biological techniques. Although an example has previously been reported of having found that a periclinal chimeric body can be produced by using a vector containing rol gene and a leaving factor (Japanese Unexamined Patent Publication No. 2002-315460), this case is a periclinal chimera of the L3 layer.

In transgenic plants, an introduced gene incorporated in a chromosome is stably transferred to progeny thereof in accordance with Mendel's laws. By then using these transgenic plants as crossing parents, new varieties of plants can be further produced by utilizing traits derived from the introduced gene.

In addition, there are concerns over transgenic plants regarding effects on the ecosystem (environment) (such as the dispersal of an introduced gene into the natural world). Known examples of technologies for preventing gene dispersal from transgenic plants to non-transformants and wild plants include (1) use of maternal inheritance, (2) use of male sterility, and (3) use of sterile seeds. The use of maternal inheritance refers to a method for preventing gene dispersal by pollen by introducing a foreign gene into a chloroplast genome that is not passed to pollen cells.

The use of male sterility refers to a method for inhibiting pollen formation or not allowing pollen to have the ability to reproduce, and makes it possible to carry out genetic isolation. For example, this method consists of tissue-specifically producing a harmful gene product using a promoter specifically expressed in male reproductive organs to inhibit pollen formation. The use of sterile seeds refers to a method for preventing both crossing or seed dispersal by directly inhibiting seed formation of a transgenic plant, and is equivalent to "terminator technology" and the like which prevents seed saving.

If it were possible to produce a transgenic plant not having an introduced gene in its germ cells, even in the case of using that transgenic plant as a pollen parent or as a seed parent, the possibility of dispersal of the introduced gene by crossing would be completely eliminated. This means that for a person engaged in cultivation of the transgenic plant in the wild or utilization of the transgenic plant industrially, the burden incurred by regulatory procedures for cultivating the transgenic plant would be reduced. In Japan, such procedures include an assessment of biodiversity effects based on the "Law Concerning the Conservation and Sustainable Use of Biological Diversity through Regulations on the Use of Living Modified Organisms" (Cartagena protocol), and include assessments based on similar laws in other countries.

Patent Document 1: Japanese Unexamined International Publication No. H10-503374

Patent Document 2: Japanese Unexamined Patent Publication No. 2002-315460

Patent Document 3: U.S. Pat. No. 5,480,789

Patent Document 4: WO 2005/017147

Patent Document 5: PCT/JP96/00348

Non-Patent Document 1: Finnegan et al., Bio/Technology, 12: 883-888, 1994

Non-Patent Document 2: Lazo et al., Bio/Technology, 9: 963-967, 1991

Non-Patent Document 3: Fujiwara et al., Plant J., 16, 421-431, 1998

Non-Patent Document 4: Mitsuhara et al., Plant Cell Physiol., 37, 49-59, 1996.

DISCLOSURE OF THE INVENTION

Thus, the present invention provides a floricultural plant such as a rose in which an introduced gene is only present in a part of the cells of the plant body, for example, is absent in germ cells.

As a result of conducting various studies to overcome the aforementioned problems, the inventors of the present invention that introduction of a foreign gene into a floricultural plant mediated by *Agrobacterium tumefaciens* can result in the regenerated floricultural plant being a chimeric plant. Moreover, it was also found that a target transgenic floricultural plant can be obtained by selecting a periclinal chimeric plant there from, thereby leading to completion of the present invention. Thus, the present invention provides a floricultural plant such as a rose in which an introduced gene is only present in a part of the cells and not present in the other cells.

The aforementioned part of the cells preferably composes a part of the cell layers. For example, the aforementioned other cells are pollen or ovule cells. More specifically, the portion of the cell layers is either the L1 layer or the L1 layer and the L3 layer. Examples of an introduced gene include genes involved in flavonoid synthesis, and particularly genes relating to flower color such as genes involved in anthocyanin synthesis.

In the case the floricutural plant is a rose, it is important that the introduced gene be, for example, a flavonoid 3',5'-hydroxylase gene derived from a plant belonging to the violet family or an aromatic acyl group transferase gene derived from a plant belonging to the snapdragon family. An example of a plant belonging to the violet family is a pansy, while an example of a plant belonging to the snapdragon family is a torenia. Examples of roses include hybrid tea rose such as rose variety WKS82, floribunda and miniature rose. Due to the effect of the introduced gene, the rose of the present invention, for example, changes its flower color to a bluish color as compared with prior to gene introduction.

In the case the floricultural plant is a carnation, the introduced gene is one or a plurality of genes such as flavonoid 3',5'-hydroxylase gene cDNA derived from salvia under the control of a promoter of a chalcone synthase gene derived from common snapdragon, a genomic gene of petunia dihydroflavonol 4-reductase, or an anthocyanin synthase gene derived from carnation. The carnation may be of the standard type or spray type. Due to the effect of the introduced gene, the carnation of the present invention, for example, changes its flower color to a bluish color as compared with prior to gene introduction.

However, the foreign gene is not limited to the genes described above, but rather may be a gene that functions in a wide range of pigment synthesis systems, and for example, may be a gene that functions in the flavonoid synthesis system. In addition, the foreign gene may be a selectable marker gene in the manner of GFP gene, NPTII gene, GUS gene or SURB gene. Moreover, the foreign gene may be a gene that encodes a transcription factor, such as a gene that encodes myb-like transcription factor, and more specifically, PHR1 gene or Psr1 gene.

In addition, the present invention also provides a tissue of the rose or other floricultural plant as described above having the same properties thereof, or a nutritive growth product thereof.

Moreover, the present invention further provides the method for producing a floricultural plant such as a rose comprising a step for introducing a foreign gene into the rose mediated by *Agrobacterium*, and selecting a rose in which the foreign gene is only present in a part of the cells thereof. The present invention further provides a method for preventing dispersal of an introduced gene into the natural world by producing a floricultural plant not having a foreign gene in the germ cells thereof as described in any of claims 3 to 27.

BRIEF DESCRIPTION OF THE DRAWINGS

FIG. 2 shows that an introduced foreign gene is only expressed in L1 layer cells and not expressed in the L2 layer or L3 layer.

BEST MODE FOR CARRYING OUT THE INVENTION

Figure 1:
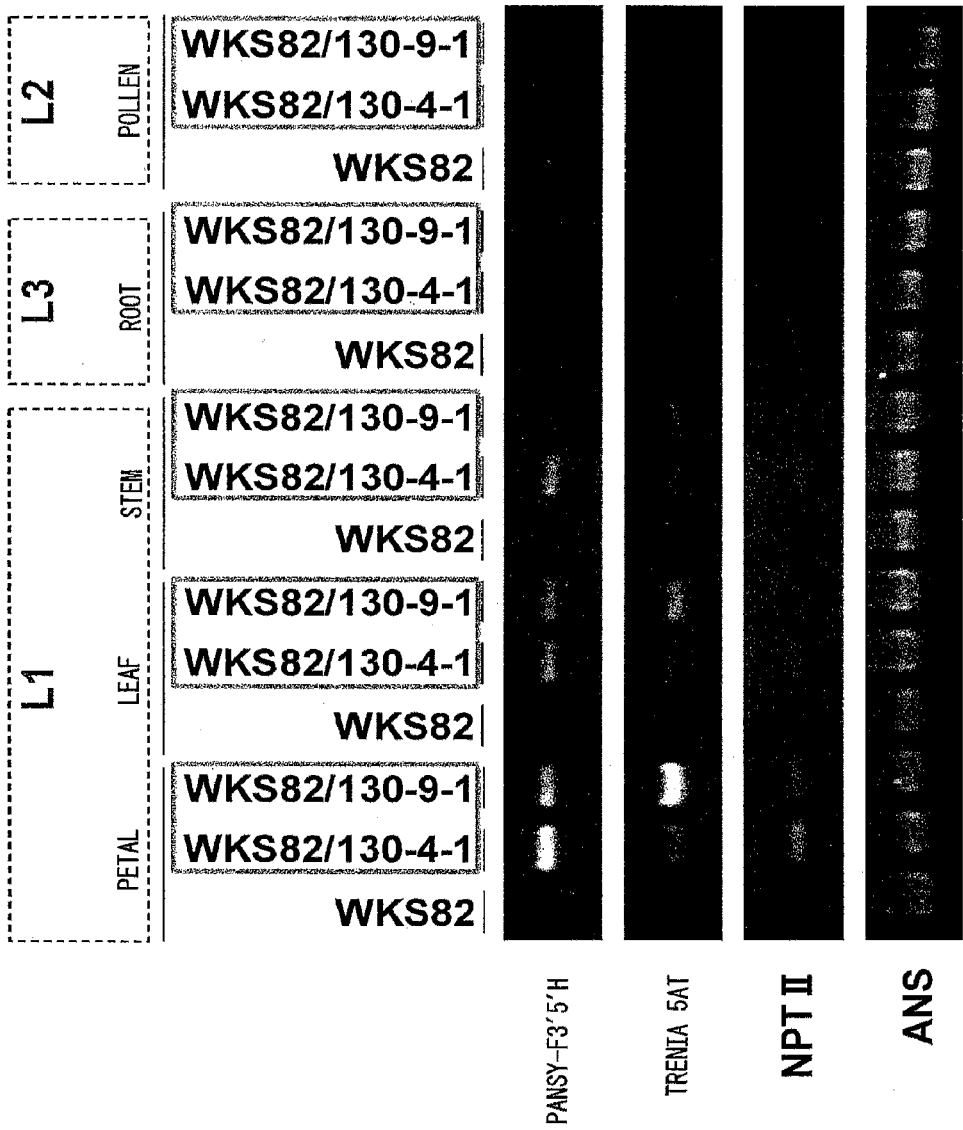
FIG. 1 is a drawing indicating the presence or absence of an introduced gene in various rose organs.

There are no particular limitations on the floricultural plant used in the present invention provided it is a floricultural plant in which a foreign gene can be introduced mediated by *Agrobacterium*. Examples of floricultural plants include rose, carnation, petunia, torenia, tobacco, verbena, Nierembergia, chrysanthemum, lily, morning glory, common snapdragon, cyclamen, orchid, prairie gentian, freesia, gerbera, gladiola, baby's breath, kalanchoe, pelargonium, geranium, tulip, rapeseed, potato, tomato, poplar, banana, eucalyptus, sweet potato, soybean, alfalfa, lupine and cauliflower. In particular, rose, carnation, petunia, torenia, tobacco, verbena and Nierembergia are preferable, with rose and carnation being able to be used particularly preferably.

The foreign gene used in the present invention is preferably a gene of an enzyme that functions in cells of the L1 layer following introduction. For example, genes related to flower color, selectable marker genes, and genes encoding transcription factors are preferable. Examples of genes related to flower color include gene of enzymes involved in flavonoid synthesis such as genes related to anthocyanin synthesis, genes encoding proteins related to aurone synthesis, genes encoding aliphatic acyl group transferases, and genes encoding flavone synthases. Examples of selectable marker genes include GFP gene and NPTII gene, GUS gene and SURB gene. Examples of genes encoding transcription factors include genes encoding MYB-like transcription factor, and more specifically, PHR1 gene and Psr1 gene. However, the present invention is not limited to the genes specifically listed here.

The rose used in the present invention may be a horticultural variety or a wild variety. In particular, commercially useful horticultural varieties (Rosa hybrida) such as hybrid tea rose, floribunda and miniature rose are preferable. There are no particular limitations on these varieties.

T-DNA composed of an expression cassette of flavonoid 3',5'-hydroxylase gene derived from pansy and an expression cassette of aromatic acyl group transferase gene NPTII derived from torenia was inserted into a rose callus mediated by *Agrobacterium*. Since the resulting transformant underwent a color change due to the action of the introduced genes, the introduced genes were suggested to be present in petal cells, and particularly in cells of the L1 layer of those petals engaged in pigment synthesis. The introduced genes were not suggested to be present in pollen cells based on PCR using as a template genomic DNA extracted from various rose organs.

In addition, in the case of having carried out a crossing test with other horticultural and wild varieties of rose using pollen obtained from the transgenic plants, there were no introduced genes detected whatsoever in the resulting seeds. On the basis of this as well, the introduced genes were suggested to not be contained in pollen cells. Moreover, the introduced genes were clearly determined to be present in the L1 cell layer only based on in situ hybridization. This finding verifies that the introduced genes are not present in germ cells such as pollen that are formed by originating in the L2 cell layer. Accordingly, a chimeric plant having an introduced gene in only a part of the cells thereof is able to be produced introducing a foreign gene in a rose callus in the manner described above.

Examples of genes of enzymes involved in flavonoid synthesis include flavonoid 3',5'-hydroxylase gene and aromatic acyl group transferase gene. Although there are no particular limitations on the sources thereof, flavonoid 3',5'-hydroxylase gene derived from a pansy or other plant of the violet family, or aromatic acyl group transferase gene derived from torenia or other plant belonging to the snapdragon family, which have been confirmed to function in roses, is preferable.

The carnation used in the present invention is preferably a commercially useful standard type or spray type. There are no particular limitations on the varieties thereof. Any of varieties such as Feeling White, Precross Doozy, Starzarl or Kortina Chanel may be used.

With respect to carnation, flavonoid 3',5'-hydroxylase gene cDNA derived from salvia under the control of a chalcone synthase gene derived from common snapdragon, petunia dihydroflavanol 4-reductase genomic gene, and anthocyanin synthase derived from carnation, SURB gene were introduced under prescribed conditions mediated by *Agrobacterium*. Since the resulting transformant underwent a color change due to the action of the introduced genes, the introduced genes were suggested to be present in petal cells, and particularly in cells of the L1 layer of petals engaged in pigment synthesis. The resulting transformant was determined to be a chimeric plant in which the introduced genes were only present in the L1 layer based on PCR using as a template genomic DNA extracted from various carnation organs.

EXAMPLES

The following provides a more detailed explanation of the present invention through examples thereof.

Example 1

Method for Introducing Genes into Rose

Numerous methods have already been reported relating to rose transformation (such as Finnegan et al., Bio/Technology, 12: 883-888, 1994, U.S. Pat. No. 5,480,789 and WO 2005/017147), and a foreign gene can be introduced into a rose in accordance with these methods.

More specifically, a rose callus derived from the leaf of a sterile seedling was immersed for 5 minutes in a broth containing *Agrobacterium tumefaciens* strain Ag10 (Lazo et al., Bio/Technology, 9: 963-967, 1991) followed by wiping off excess broth with sterile filter paper, transplanting to a subculturing medium and co-cultivating in a dark location for 2 days.

Subsequently, after washing with MS liquid medium containing 400 mg/l of carbenicillin, the rose callus was transplanted to a selection/disinfection medium in which 50 mg/l of kanamycin and 200 mg/l of carbenicillin were added to subculturing medium. Transplantation and culturing were repeated on the portion that grew normally without being inhibited in the selection medium to select a kanamycin-resistant callus.

The transformed callus that exhibited kanamycin resistance was cultured in redifferentiation medium containing 50 mg/l kanamycin and 200 mg/l of carbenicillin to obtain kanamycin-resistant shoots. The resulting shoots were acclimated after causing to form roots in 1/2MS medium (not containing kanamycin). After potting the acclimated individuals, the acclimated individuals were cultivated in a closed system greenhouse and allowed to bloom. Subsequently, the individuals were maintained and allowed to grow by ordinary vegitative propagation (grafting).

Example 2

Construction of Binary Vector pSPB130

Anthocyanin can be stabilized and its blue color can be made more intense by modifying the anthocyanin with an aromatic acyl group (see, for example, PCT/JP96/00348). The following experiment was conducted for the purpose of producing an acylated delphinidine-type anthocyanin.

Total RNA was obtained from the petals of torenia (trade name: Summer Wave (trademark)) after which polyA+RNA was prepared there from. A cDNA library using λZAPII (Stratagene) as a vector was prepared from this polyA+RNA using a directional cDNA library production kit (Stratagene) according to the method recommended by the manufacturer.

Since the major anthocyanin of torenia has the glucose at position 5 modified by an aromatic acyl group (Suzuki et al., Molecular Breeding, 6, 239-246, 2000), anthocyanin acyl group transferase is expressed in torenia petals. Anthocyanin acyl group transferase retains the amino acid sequence of Asp-Phe-Gly-Trp-Gly-Lys (SEQ ID NO: 13), and anthocyanin acyl group transferase gene can be acquired by using a synthetic DNA corresponding thereto as a primer (PCT/JP96/00348).

More specifically, PCR was carried out using Taq polymerase (Takara, Japan) under conditions recommended by the manufacturer using 10 ng of single-strand DNA synthesized during production of the torenia cDNA library as a template, and using 100 ng of ATC primer (5'-GA(TC)TT(TC)GGITGGGGIAA-3', wherein I represents inosine and (TC) represents either represents T or C) (SEQ ID NO. 1) and 100 ng of oligo dT primer (5'-TTTTTTTTTTTTTTTTTCTCGAG-3') (SEQ ID NO. 2) as primers. PCR was carried out for 25 cycles of reactions consisting of 1 minute at 95° C., 1 minute at 55° C. and 1 minute at 72° C. The resulting approximately 400 bp DNA fragment was recovered by Gene Clean II (BIO 101 Inc.) according to the method recommended by the manufacturer and subcloned to pCR-TOPO.

When the base sequence thereof was determined, a sequence was observed that was homologous to gentian acyl group transferase gene (Fujiwara et al., Plant J., 16, 421-431, 1998). Furthermore, the base sequence was determined using the Sequencer 310 or 377 (Applied Biosystems) according to the Diprimer Method (Applied Biosystems).

This DNA fragment was then labeled with DIG using a DIG labeling and detection kit (Nippon Roche), and the torenia cDNA library was screened by plaque hybridization according to the method recommended by the manufacturer. Twelve of the resulting clones yielding a positive signal were randomly selected and plasmids were recovered there from followed by determination of base sequences. These sequences demonstrated good homology with anthocyanin acyl group transferase. The entire base sequence was determined for cDNA contained in the clone designated pTAT7 (SEQ ID NO. 3, coded amino acid sequence disclosed as SEQ ID NO: 18).

After digesting pBE2113-GUS (Mitsuhara et al., Plant Cell Physiol., 37, 49-59, 1996) with SacI, the ends were smoothened followed by insertion of an 8 by XhoI linker (Takara). An approximately 1.7 kb DNA fragment obtained by digesting pTAT7 with BamHI and XhoI was inserted into the BamHI and XhoI sites of this plasmid to obtain pSPB120. After digesting pSPB120 with SnaBI and BamHI, the ends were smoothened followed by ligation to obtain pSPB120'. On the other hand, a plasmid pCGP1961, containing F3',5' H#40 cDNA derived from pansy, was completely digested with BamHI followed by partial digestion with XhoI and recovery of the resulting approximately 1.8 kb DNA fragment which was then ligated with pUE5H digested with BamHI and XhoI. The resulting plasmid was designated pUEBP40.

Figure 3:
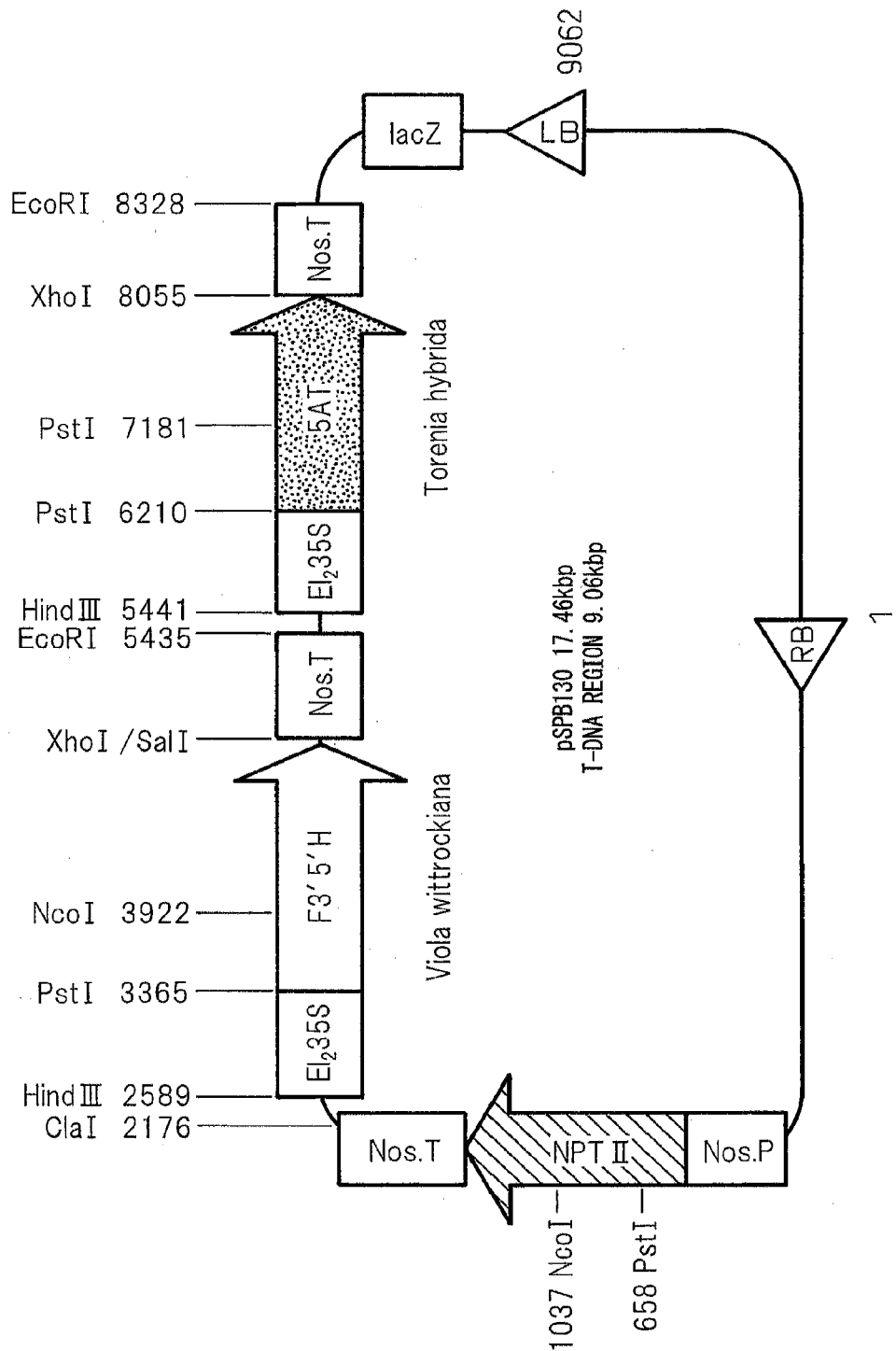
FIG. 3 indicates the structure of a binary vector pSPB130 used in Example 2.

After digesting pUEBP40 with SnaBI and BamHI, the ends were smoothened followed by ligation to obtain pUEBP40'. An approximately 2.7 kb DNA fragment obtained by partially digesting pUEBP40 with HindIII was recovered and ligated with a DNA fragment partially digested with HindIII. Among the resulting plasmids, the binary vector in which neomycin phosphotransferase gene, pansy F3'5'H #40 and torenia 5AT gene were respectively ligated in the same direction in order starting from the right border of the binary vector was designated as pSPB130 (FIG. 3). This plasmid constitutively expresses pansy F3'5'H #40 gene and 5AT gene in plants, and is designed to transcribe the genes petal-specifically. This plasmid was introduced into *Agrobacterium tumefaciens* strain Ag10.

Example 3

Introduction of Pansy F3'5'H #40 Gene and Torenia Anthocyanin 5-Acyl Group Transferase Gene into WKS82

The pSPB130 was introduced into a light violet-colored rose "WKS82", and 89 transformants were obtained. Accumulation of delphinidin was confirmed in all 44 transformants that underwent pigment analysis. The delphinidin content was a maximum of 91% (mean: 49%). Flower color changed from 186d of the RHS color chart (greyed-purple group) to 80c (purple-violet group). The analysis values of representative transformants are shown in the following tables.

TABLE 1

| Plant No. | Acyl (%) | Del (%) | Del (mg/g) | Cya (mg/g) | Pel (mg/g) | M (mg/g) | Q (mg/g) | K (mg/g) |
|---|---|---|---|---|---|---|---|---|
| WKS82 control | 0.0 | 0.0% | 0.000 | 0.074 | 0.000 | 0.000 | 2.400 | 0.196 |
| 1 | 10.5 | 52.3% | 0.055 | 0.050 | 0.000 | 0.430 | 0.883 | 0.083 |
| 2 | 15.9 | 62.5% | 0.091 | 0.054 | 0.000 | 0.570 | 0.549 | 0.030 |
| 3 | 15.9 | 36.6% | 0.044 | 0.076 | 0.000 | 0.622 | 2.221 | 0.102 |
| 4 | 6.8 | 40.0% | 0.023 | 0.034 | 0.000 | 0.247 | 0.986 | 0.172 |
| 5 | 15.0 | 82.9% | 0.087 | 0.018 | 0.000 | 5.451 | 0.403 | 0.042 |
| 6 |  | 89.7% | 0.072 | 0.008 | 0.000 | 0.853 | 0.163 | 0.062 |
| 7 | 9.5 | 89.5% | 0.101 | 0.012 | 0.000 | 0.719 | 0.144 | 0.019 |
| 8 | 14.7 | 11.4% | 0.012 | 0.090 | 0.000 | na | na | na |
| 9 | 11.6 | 29.3% | 0.024 | 0.059 | 0.000 | na | na | na |
| 10 | 8.7 | 15.2% | 0.010 | 0.053 | 0.000 | na | na | na |
| 11 | 7.9 | 59.0% | 0.046 | 0.032 | 0.000 | 0.580 | 0.619 | 0.022 |
| 12 | 8.5 | 55.6% | 0.060 | 0.048 | 0.000 | 1.318 | 1.615 | 0.165 |
| 13 | 13.9 | 42.3% | 0.026 | 0.035 | 0.000 | 0.603 | 1.094 | 0.052 |
| 14 | 10.1 | 10.3% | 0.008 | 0.073 | 0.000 | na | na | na |
| 15 | 10.6 | 18.8% | 0.018 | 0.079 | 0.000 | na | na | na |
| 16 | 9.3 | 11.7% | 0.009 | 0.066 | 0.000 | na | na | na |
| 17 | 14.3 | 76.2% | 0.112 | 0.035 | 0.000 | 3.741 | 1.587 | 0.377 |
| 18 | 12.7 | 76.7% | 0.101 | 0.031 | 0.000 | 1.608 | 0.656 | 0.075 |
| 19 | 9.8 | 71.7% | 0.057 | 0.022 | 0.000 | 1.403 | 0.455 | 0.041 |
| 20 | 5.3 | 14.1% | 0.011 | 0.068 | 0.000 | 0.132 | 2.999 | 0.720 |
| 21 | 3.5 | 18.5% | 0.008 | 0.035 | 0.000 | na | na | na |
| 21 | 7.7 | 23.1% | 0.017 | 0.055 | 0.000 | 0.141 | 0.929 | 0.034 |
| 22 | 5.4 | 19.0% | 0.015 | 0.065 | 0.000 | 0.297 | 4.128 | 1.350 |

Del: delphinidin, Cya: cyanidin, Pel: pelargonidin, M: myricetin, Q: quercetin, K: kaempferol, Del(%): percentage of delphinidin in total anthocyanin, Acyl(%): percentage of acylated pigment in total anthocyanin, na: not analyzed.

TABLE 2

| Plant No. | Acyl (%) | Del (%) | Del (mg/g) | Cya (mg/g) | Pel (mg/g) | M (mg/g) | Q (mg/g) | K (mg/g) |
|---|---|---|---|---|---|---|---|---|
| 23 | 1.1 | 42.1% | 0.036 | 0.050 | 0.000 | 0.609 | 2.929 | 0.679 |
| 24 | 22.7 | 91.0% | 0.079 | 0.008 | 0.000 | 0.964 | 0.218 | 0.018 |
| 25 | 6.1 | 61.3% | 0.048 | 0.030 | 0.000 | 0.490 | 0.468 | 0.029 |
| 26 | 8.7 | 91.3% | 0.097 | 0.009 | 0.000 | 2.053 | 0.339 | 0.123 |
| 27 | 9.4 | 59.9% | 0.060 | 0.040 | 0.000 | 1.537 | 1.631 | 0.422 |
| 28 | 5.5 | 51.2% | 0.040 | 0.038 | 0.000 | 0.688 | 0.723 | 0.038 |
| 29 | 5.1 | 61.4% | 0.056 | 0.032 | 0.003 | 0.637 | 0.537 | 0.087 |
| 30 | 7.0 | 53.3% | 0.037 | 0.032 | 0.000 | 0.706 | 1.032 | 0.051 |
| 31 | 5.7 | 58.1% | 0.071 | 0.051 | 0.000 | 1.592 | 1.478 | 0.220 |
| 32 | 4.3 | 64.6% | 0.092 | 0.050 | 0.000 | 0.849 | 0.753 | 0.035 |
| 33 | 6.4 | 61.7% | 0.042 | 0.026 | 0.000 | 0.477 | 0.468 | 0.023 |
| 34 | 8.9 | 58.8% | 0.048 | 0.034 | 0.000 | 0.646 | 0.928 | 0.063 |
| 35 | 6.2 | 11.6% | 0.007 | 0.057 | 0.000 | 0.094 | 1.132 | 0.066 |
| 36 | 7.1 | 51.2% | 0.038 | 0.036 | 0.000 | 0.911 | 1.135 | 0.079 |
| 37 | 5.8 | 50.8% | 0.029 | 0.028 | 0.000 | 0.868 | 1.105 | 0.096 |
| 38 | 5.5 | 47.0% | 0.027 | 0.023 | 0.007 | 1.366 | 1.632 | 0.105 |
| 39 | 4.9 | 67.0% | 0.044 | 0.022 | 0.000 | 0.795 | 0.586 | 0.051 |
| 40 | 0.0 | 61.1% | 0.053 | 0.033 | 0.000 | 1.310 | 1.466 | 0.259 |
| 41 | 9.6 | 71.0% | 0.074 | 0.030 | 0.000 | 0.460 | 0.337 | 0.023 |
| 42 | 1.2 | 27.6% | 0.009 | 0.024 | 0.000 | na | na | na |
| 43 | 5.2 | 13.8% | 0.013 | 0.078 | 0.000 | na | na | na |

Del: delphinidin, Cya: cyanidin, Pel: pelargonidin, M: myricetin, Q: quercetin, K: kaempferol, Del(%): percentage of delphinidin in total anthocyanin, Acyl(%): percentage of acylated pigment in total anthocyanin, na: not analyzed.

Example 4

Confirmation of Presence of Introduced Gene in Each Organ

Genomic DNA was extracted from petals, leaves, stems, roots and pollen of "WKS82" (to be referred to as the "host") and recombinants nos. 5 and 24 produced in Example 3(WKS82/130-4-1 and WKS82/130-9-1, to be referred to as "recombinants") using DNeasy Plant Mini Kit (Qiagen) in accordance with the method recommended by the manufacturer. Introduced genes (pansy F3'5'H gene (SEQ ID NO. 4, coded amino acid sequence disclosed as SEQ ID NO: 19), torenia 5AT gene (SEQ ID NO. 3, coded amino acid sequence disclosed as SEQ ID NO: 18) and *E. coli* NPTII gene) were amplified by PCR with Takara Ex Taq (Takara) using the extracted DNA as templates.

Moreover, rose anthocyanin synthase (ANS) gene was amplified as an endogenous control. The PCR reaction conditions consisted of repeating 25 cycles consisting thermal denaturation for 5 minutes at 94° C., for 30 seconds at 94° C., for 30 seconds at 55° C. and for 1 minute at 72° C., followed by an elongation reaction for 7 minutes at 72° C. The resulting amplification products were eletrophoresed in agarose gel and amplified fragments were detected by ethidium bromide staining.

Furthermore, BP40-F2 and BP40-R3 were used as primers for amplification of pansy F3'5'H gene, TAT7-50F and TAT7-R1 were used for amplification of torenia 5AT, NPTII-F and NPTII-R were used for amplification of NTPII gene, and RhANS69-r1 and RhANS69-m1 were used for amplification of ANS gene.

Pansy F3'5'H gene-specific primers:

```
BP40-F2:
5'-GAG CTA GGC CAC ATG CTT A-3'    (SEQ ID NO. 5)

BP40-R3:
5'-CTT TGC GCT CAT GAC TCG T-3'    (SEQ ID NO. 6)
```

Torenia 5AT gene-specific primers:

```
                                   (SEQ ID NO. 7)
TAT7-50F:   5'-AAC AAT ATG TGC AGT CCT CGA A-3'

(SEQ ID NO. 8)
TAT7-R1:    5'-AAC TCG CAT GCG CAA CTA C-3'
```

NPTII gene-specific primers:

```
                                   (SEQ ID NO. 9)
NPTII-F:    5'-GAT TGA ACA AGA TGG ATT GCA CGC-3'

(SEQ ID NO. 10)
NPTII-R:    5'-CGA AGA ACT CCA GCA TGA GAT CCC-3'
```

ANS gene-specific primers:

```
                                   (SEQ ID NO. 11)
RhANS69-r1: 5'-TTT GAT CTT CCC ATT GAG C-3'

(SEQ ID NO. 12)
RhANS69-m1: 5'-TCC GCG GTG GGA AGA TCC CC-3'
```

As a result of analyzing by PCR, although the introduced genes were detected in the petals, leaves and stems of the recombinants, these introduced genes were not detected in the genomes of the roots or pollen. The results are shown in Table 3 and FIG. 1.

In addition, petals, epidermal systems of the leaves and stems, sepal, stamen and pistil are known to be derived from the L1 layer and L2 layer, pollen and oocytes from the L2 layer, and the internal tissue of leaves and stems along with roots from the L3 layer. Since introduced genes were not detected in the genomes of the roots and pollen, these recombinants were suggested to be chimeric plants in which introduced genes were only present in the L1 layer.

TABLE 3

Presence of Introduced Gene in Various Organs of Recombinants

| Detected Gene | Presence of Introduced Gene | | | | |
|---|---|---|---|---|---|
| | Petal | Leaf | Stem | Root | Pollen |
| Pansy F3'5'H | + | + | + | − | − |
| Torenia 5AT | + | + | + | − | − |
| NPTII | + | + | + | − | − |

Example 5

Artificial Crossing with Horticultural Varieties (in a Greenhouse)

After removal of anther and bagging horticultural varieties immediately prior to blooming in accordance with ordinary methods, pollen of the host or recombinant no. 24 produced in Example 3 (WKS82/130-9-1, to be referred to as the recombinant) cultivated in a greenhouse in the morning on a sunny day was adhered at the time the stamen had adequately matured. Subsequently, the plants were again bagged to prevent adhesion of other pollen and then investigated for the presence of seed formation. Furthermore, the pollen was fresh pollen obtained by recovering the anther prior to dehiscence and then allowing to stand at room temperature for 1 day in a desiccator containing silica gel followed by recovering from the anther that underwent dehiscence on the following day. The female parents consisted of a Grandiflora perpetual rose variety known as "Queen Elizabeth" and a Floribunda perpetual rose variety known as "Gold Bunny".

The presence of seed formation was confirmed one month or more after crossing for fruit that had not dropped physiologically and in which seed setting was observed. Moreover, in order to confirm the passing on of introduced genes to the next generation for seeds obtained by crossing with the recombinant, genomic DNA was extracted from the resulting seeds using Nucleon Phytopure for Plant DNA Extraction Kit (Amersham Biosciences), and after further amplifying with the REPLI-g Kit (Qiagen), the introduced gene (pansy F3'5'H gene) was detected by PCR.

The results are shown in Table 4. There were hardly any differences observed in the seed-set rates between the host and the recombinant. Moreover, as a result of analyzing seeds obtained by crossing with the recombinant, there were no introduced genes detected in the seeds. On the basis of these findings, although there were no differences in pollen fertilizing ability between the host and recombinant, for reasons such as introduced gene not being contained in pollen cells of the recombinant, the introduced gene was suggested to not be passed to the next generation.

Example 6

Artificial Crossing with Horticultural Varieties (Outdoors)

After removal of anthers and bagging horticultural varieties immediately prior to blooming in accordance with ordinary methods, pollen of the host or recombinant no. 24 produced in Example 3 (WKS82/130-9-1, to be referred to as the recombinant) cultivated outdoors in the morning on a sunny day was adhered at the time the stamen had adequately matured. Subsequently, the plants were again bagged to prevent adhesion of other pollen and then investigated for the presence of seed formation. Furthermore, the pollen was fresh pollen obtained by recovering the anther prior to dehiscence and then allowing to stand at room temperature for 1 day in a desiccator containing silica gel followed by recovering from the anther that underwent dehiscence on the following day.

The female parents consisted of a Grandiflora perpetual rose variety known as "Queen Elizabeth" and a Floribunda perpetual rose variety known as "Gold Bunny".

The presence of seed formation was confirmed three months or more after crossing for fruit that had not dropped physiologically and in which seed setting was observed. Moreover, seeds recovered from crossing with the recombinant were recovered and treated at a low temperature of 4° C. for 3 months followed by seeding. In order to confirm the passing on of introduced genes to the next generation for these seeds, genomic DNA was extracted from leaves of the resulting seedlings using the DNeasy Plant Mini Kit (Qiagen) followed by detection of the introduced gene (pansy F3'5'H gene) by PCR. Furthermore, rose glyceraldehyde-3-phosphate dehydrogenase (GAPDH) gene was detected as the intrinsic control gene.

In addition, although germination is normally observed in about one month in the case of treating the seeds at low temperatures, germination was only observed in a portion of the seeds even after three months. Therefore, a portion of the seeded seeds that did not germinate were re-recovered, and a similar analysis was carried out using those seeds. Genomic DNA was extracted from the re-recovered seeds using Nucleon Phytopure for Plant DNA Extraction Kit (Amersham Biosciences), and after amplifying the genomic DNA with the REPLI-g Kit (Qiagen), the introduced gene (pansy F3'5'H gene) was detected by PCR.

The results are shown in Tables 5 and 6. There were hardly any differences observed in the seed-set rates between the host and the recombinant. Moreover, although seedlings obtained by crossing with the recombinant were analyzed by PCR, introduced genes derived from the recombinant were

TABLE 4

Artificial Pollination with Horticultural Varieties

| | Host (WKS82) | | Recombinant No. 24 (WKS82/130-9-1) | | | |
|---|---|---|---|---|---|---|
| | | | | | No. of seeds in | |
| | No. of seeds set/no. of crossed flowers | Seed-set rate (%) | No. of seed sets/no. of crossed flowers | Seed-set rate (%) | which introduced gene detected/no. of seed analyzed | Introduced gene detection rate (%) |
| Queen Elizabeth | 19/20 | 95 | 20/20 | 100 | 0/94 | 0 |
| Cold Bunny | 16/20 | 80 | 14/20 | 70 | 0/94 | 0 | not detected in the seedlings. Moreover, there were also no introduced genes derived from the recombinant detected in the seeds. On the basis of these findings, although there were no differences in pollen fertilizing ability between the host and recombinant, for reasons such as introduced gene not being contained in pollen cells of the recombinant, the introduced gene was suggested to not be passed to the next generation.

TABLE 5

Seed-set Rates with Horticultural Varieties by Artificial Pollination and Detection Rates of Introduced Gene in Germinating Individuals

| | Host (WKS82) | | | Recombinant No. 24 (WKS82/130-9-1) | | | | |
|---|---|---|---|---|---|---|---|---|
| | No. of seeds set/no. of crossed flowers | Seed-set rate (%) | Total no. of seeds | No. of seeds set/no. of crossed flowers | Seed-set rate (%) | Total no. of seeds | No. of individuals in which introduced gene detected/no. of germinating individuals | Introduced gene detection rate (%) |
| Queen Elizabeth | 27/41 | 65.8 | 262 | 19/42 | 45.2 | 192 | 0/4 | 0.0 |
| Gold Bunny | 14/64 | 21.8 | 174 | 15/60 | 25.0 | 150 | 0/9 | 0.0 |

TABLE 6

Detection Rates of Introduced Gene in Seeds Obtained by Artificial Pollination with Horticultural Varieties

| | Recombinant No. 24 (WKS82/130-9-1) | | |
|---|---|---|---|
| | No. of seeds recovered[1] | No. of seeds in which introduced gene detected/no. of seeds analyzed[2] | Introduced gene detection rate (%) |
| Queen Elizabeth | 155 | 0/33 | 0.0 |
| Gold Bunny | 122 | 0/37 | 0.0 |

*[1,2] Differences in the numbers of seeds recovered and numbers of analyzed seeds occurred because those seeds that were hollow that prevented extraction of DNA or for which amplification of the control gene was not observed in PCR analysis were excluded from the analyses.

Example 7

Artificial Crossing with Wild Varieties (Outdoors)

After removal of anther and bagging horticultural varieties immediately prior to blooming in accordance with ordinary methods, pollen of the host or recombinant no. 24 produced in Example 3 (WKS82/130-9-1, to be referred to as the recombinant) cultivated outdoors in the morning on a sunny day was adhered at the time the stamen had adequately matured.

Subsequently, the plants were again bagged to prevent adhesion of other pollen and then investigated for the presence of seed formation. Furthermore, the pollen was fresh pollen obtained by recovering the anther prior to dehiscence and then allowing to stand at room temperature for 1 day in a desiccator containing silica gel followed by recovering from the anther that underwent dehiscence on the following day.

The female parents consisted of wild varieties known as R. multiflora Thunb. ex Murray, R. wichuraiana Crep. and R. rugosa Thunb. ex Murray).

The presence of seed formation was confirmed two months or more after crossing for fruit that had not dropped physiologically and in which seed setting was observed. Moreover, the resulting seeds were recovered and subjected to treatment at a low temperature of 4° C. for 3 months followed by seeding. In order to confirm the presence of crossing with the host or recombinant and the passing on of introduced genes to the next generation, genomic DNA was extracted from leaves of the resulting seedlings using the DNeasy Plant Mini Kit (Qiagen) followed and analyzed by PCR. A gene involved in perpetuality (KSN gene) was used as an indicator for the presence of crossing with the host or recombinant, while an introduced gene derived from the recombinant in the form of pansy F3'5'H gene was used as an indicator for the presence of passing on the introduced gene. Furthermore, rose GAPDH gene was used as an intrinsic control gene.

The KSN gene is formed as a result of an approximately 9 kb transposon being inserted into the ksn gene (having a function that maintains the shoot meristem) of seasonal roses, and since expression of this gene is inhibited as a result thereof causing inhibition of the formation of flower buds on the shoot meristem to be cancelled, flower bud formation is promoted which is reported to cause the flower to become perpetual[1]. Horticultural varieties are homozygous for the KSN gene. On the other hand, seasonal wild varieties are homozygous for the ksn gene. Thus, in wild varieties (seasonal varieties), the KSN gene is thought to only be detected in the case it has been crossed with a horticultural variety.

In addition, although germination is normally observed in about one month in the case of treating the seeds at low temperatures, germination was only observed in a portion of the seeds even after three months.

Therefore, a portion of the seeded seeds that did not germinate were re-recovered, and a similar analysis was carried out using those seeds. Genomic DNA was extracted from the re-recovered seeds using Nucleon Phytopure for Plant DNA Extraction Kit (Amersham Biosciences), and after amplifying the genomic DNA with the REPLI-g Kit (Qiagen), the presence of crossing with the host or recombinant and the presence of passing on of the introduced gene was detected by PCR.

The results are shown in Tables 7 and 8. Seed-set rates were extremely low in the case of using either the recombinant for each of the pollen parents. Although the resulting seedlings were analyzed by PCR, pollination between the host or recombinant and the wild varieties was observed, but the introduced gene derived from the recombinant was not detected. Moreover, seeded seeds that did not germinate were re-recovered, and when the seeds were observed for development, nearly all the seeds were empty, and normal embryos were only able to be confirmed in an extremely small number of the seeds. Although these were also similarly analyzed by PCR, pollination was confirmed between the host or recombinant and the wild varieties even though an introduced gene derived from the recombinant was not detected. On the basis of these findings, for reasons such as introduced gene not being contained in pollen cells of the recombinant, the introduced gene was thought to not be passed to the next generation.

Accordingly, since an introduced gene is not contained in pollen cells of the recombinant even in the case of pollination between the recombinant and wild varieties (*R. multiflora* Thunb. ex Murray, *R. wichuraiana* Crep. and *R. rugosa* Thunb. ex Murray), the introduced gene was suggested to not have the possibility of being passed to the next generation.

Furthermore, normal embryos were unable to be confirmed for any of the seeds of *R. wichuraiana* Crep.

Example 8

In Situ Hybridization

In situ hybridization was carried out in order to investigate the localization of an introduced gene in more detail. After severing a bud measuring about 5 mm in size in the vertical direction, the severed portions were fixed by immersing in a formaldehyde fixing solution. Next, the fixing solution was sequentially replaced with ethanol solutions ranging from 50% to 100% to dehydrate the severed portions followed by replacement (clarification) with 25% lemozol. The sections were subsequently gradually immersed in paraffin and embedded therein. The embedded samples were sliced with a microtome and adhered to slide glasses. After hydrating the

TABLE 7

Seed-set Rates of Wild Varieties (*R. multiflora* Thunb. ex Murray, *R. wichuraiana* Crep. and *R. rugosa* Thunb. ex Murray) Obtained by Artificial Pollination and Detection Rates of Introduced Gene in Germinated Individuals

|  | Host (WSK82) | | | | | Recombinant No. 24 (WKS82/130-9-1) | |
| --- | --- | --- | --- | --- | --- | --- | --- |
|  | No. of seeds set/no. of crossed flowers | Seed-set rate (%) | Total no. of seeds | No. of pollinated individuals/no. of germinations | Pollination rate | No. of seeds set/no. of crossed flowers | Seed-set rate (%) |
| *R. multiflora* Thunb. ex Murray | 18/251 | 7.1 | 27 | 1/2 | 50.0 | 34/255 | 13.3 |
| *R. wichuraiana* Crep. | 23/260 | 8.8 | 44 | 1/1 | 100.0 | 14/261 | 5.4 |
| *R. rugosa* Thunb. ex Murray | 2/74 | 2.7 | 263 | 0/0 | — | 4/71 | 5.6 |

|  | Recombinant No. 24 (WKS82/130-9-1) | | | | |
| --- | --- | --- | --- | --- | --- |
|  | Total no. of seeds | No. of pollinated individuals/no. of germinations | Pollination rate | No. of individuals in which introduced gene detected/No. of germinations | Introduced gene detection rate (%) |
| *R. multiflora* Thunb. ex Murray | 59 | 1/4 | 25.0 | 0/4 | 0.0 |
| *R. wichuraiana* Crep. | 44 | 0/0 | — | 0/0 | — |
| *R. rugosa* Thunb. ex Murray | 283 | 0/0 | — | 0/0 | — |

TABLE 8

Detection Rates of Introduced Gene in Seeds Obtained by Artificial Pollination of Wild Varieties ((*R. multiflora* Thunb. ex Murray, *R. wichuraiana* Crep. and *R. rugosa* Thunb. ex Murray)

|  | Host (WKS82) | | | Recombinant No. 24 (WKS82/130-9-1) | | | | |
| --- | --- | --- | --- | --- | --- | --- | --- | --- |
|  | No. of seeds recovered[1] | No. of pollinated seeds/ No. of seeds analyzed[2] | Pollination rate (%) | No. of seeds recovered[1] | No. of pollinated seeds/ No. of seeds analyzed[2] | Pollination rate (%) | No. of seeds in which introduced gene detected/No. of seeds analyzed | Introduced gene detection rate (%) |
| *R. multiflora* Thunb. ex Murray | 23 | 11/12 | 91.7 | 44 | 8/8 | 100.0 | 0/8 | 0.0 |
| *R. wichuraiana* Crep. | 43 | 0/0 | — | 44 | 0/0 | — | 0/0 | — |
| *R. rugosa* Thunb. ex Murray | 257 | 30/33 | 90.9 | 281 | 24/26 | 92.3 | 0/26 | 0.0 |

*[1,2] Differences in the numbers of seeds recovered and numbers of analyzed seeds occurred because those seeds that were hollow that prevented extraction of DNA or for which amplification of the control gene was not observed in PCR analysis were excluded from the analyses.

slide glasses, treating with Proteinase K and carrying out pretreatment in the form of acetylation and the like, the samples were dehydrated and dried. DIG-labeled probes (antisense and sense probes of BP40, TAT, NPTII and each gene) were dissolved in a hybridization solution, placed on the dried slide glasses and allowed to react. Following hybridization, the slide glasses were washed followed by detection of DIG.

As shown in the photographs of FIG. 2, the introduced genes were only expressed in cells of the L1 layer, while expression was not observed in cells of the L2 or L3 layers. On the basis thereof, since the introduced genes are only present in the L1 layer but not in the L2 layer or L3 layer, the introduced genes were verified to not be present in germ cells (pollen cells and ovule cells) that develop from the L2 layer.

Example 9

Production and Analysis of Transgenic Carnation

A carnation was produced in which an introduced gene was present only in the L1 layer.

The transgenic carnation was produced in the manner described below by gene introduction mediated by *Agrobacterium*. A plasmid pCGP2442 (described in U.S. patent application Ser. No. US/988,293 filed on Nov. 15, 2007) contained in the T-DNA region thereof flavonoid 3',5'-hydroxylase gene cDNA under the control of a promoter of a chalcone synthase gene derived from common snapdragon, a genomic gene of petunia dihydroflavonol 4-reductase, an anthocyanin synthase gene derived from carnation, and a transformation selectable marker in the form of tobacco acetolactate synthase gene SURB cDNA under the control of cauliflower mosaic virus 35S promoter. This plasmid was introduced into *Agrobacterium* using the method described in Japanese Unexamined International Patent Publication No. H11-505116 followed by further introducing into Carnation variety Cortina Chanel. Delphinidin was detected in petals of the resulting transgenic carnation that is not contained in natural carnations. This indicates that the introduced gene at least functions in the epidermal cells of the petals. A detailed analysis was conducted on one strain thereof (strain 19907). In addition, as a result of extracting chromosomal DNA from this strain 19907 and analyzing by southern hybridization using a gene of the aforementioned pCGP2442 T-DNA as a probe, the introduced gene was confirmed have been inserted into a chromosome.

A tissue culture was produced by planting shoots of strain 19907 and strain 26898 in hormone-free MS solid medium containing 5 µg/L of Glean. When the shoots were observed for the presence of root formation for 4 to 5 weeks, although strain 26898 formed roots, strain 19907 did not.

Next, leaf sections obtained from strain 19907, strain 26898 and the Kortina Chanel variety were cultured for 5 weeks in half-strength MS solid medium with 0.5 mg/L IAA and containing 5 µg/L of Glean, and half-strength MS solid medium with 0.5 mg/L IAA not containing Glean. The leaf sections of strain 19907 and the Kortina Chanel variety that were cultured in medium containing 5 µg/L of Glean became brown. The leaf section obtained from strain 26898 was green and was observed to have formed roots.

Chromosomal DNA was extracted from the leaves and roots of strain 19907 using the DNeasy Plant Mini Kit (Qiagen). PCR was then carried out using 100 ng of this DNA as a template and using synthetic primers for amplifying SuRB gene (#960: 5'-ATT TCC GCC TCA TTA GAA GG-3' (SEQ ID NO: 14), #1468: 5'-GCC TCA TGT TTC CAT TTG TCG-3' (SEQ ID NO: 15)). After carrying out the reaction for 15 minutes at 95° C. at reaction volume of 25 µl using Hot Star Taq, the reaction was further carried out for 35 cycles with one cycle consisting of 1 minute at 96° C., 30 seconds at 52° C. and 2 minutes at 72° C., followed by finally carrying out the reaction for 7 minutes at 72° C. When the reaction product was analyzed by agarose gel electrophoresis, although the band for SURB was observed in the case of using leaf DNA as a template, the SURB band was not observed in the case of using root DNA.

Leaves are known to be composed of L1, L2 and L3 cells, while roots are known to be composed of L2 and L3 cells. On the basis of the above results, in the case of strain 19907, the introduced gene was present in L1 cells, but not present in L2 and L3 cells, or in other words, strain 19970 was determined to be a chimeric plant in which the introduced gene is only present in the L1 layer.

Example 10

Study of Potential for Application of the Technology of the Present Invention to Various Plants (1) Example of Infection into Petunia Using petunia for the floricultural plant, a gene involved in flavonoid synthesis was introduced as a foreign gene.

A DNA fragment (approx. 2.0 kb), linking butterfly pea F3'5'H cDNA and an nos terminator, was recovered from an El$_2$35S promoter sequence, having two repeating enhancer sequences upstream from a cauliflower mosaic virus (CaMV) 35S promoter (Plant Cell Physiol., 37, 49-59 (1996)), and pSPB748 (Plant Cell Physiol., 43, s277 (2002)), obtained by introducing a butterfly pea F3'5'H cDNA sequence (described in Patent Application No. WO 2004/020637) and a nopaline synthase (nos) terminator sequence into a binary vector pBinPlus (Transgenic Research, 4, 288-290 (1995)), by digesting with BamHI and partially digesting with EcoRI, followed by introducing into a BamHI/EcoRI site of pBluescriptII (sk−) (Stratagene) to obtain a plasmid pB-Bn. A gene cassette consisting of a GUS gene and an nos terminator was extracted with XbaI and KpnI from a 6xXRE promoter sequence having six repetitions of mouse xenobiotic responsive element (XRE), and pBlueSXXREGUS (Kodama (2003), Molecular mechanisms of chemical-inducible gene expression in higher plants for monitoring and remediation of environmental contaminants, Diss.), obtained by introducing a GUS gene and an nos terminator into pBluescriptII (ks+) (Stratagene), followed by introducing to the same site a DNA fragment (approx. 2.0 kb) linking butterfly pea F3'5'H and nos terminator excised from pB-Bn by digesting with XbaI and KpnI to obtain pB-X6Bn. A gene cassette (2.2 kb) consisting of 6xXRE promoter sequence, butterfly pea F3',5'H cDNA and an nos terminator sequence, excised by digesting pB-X6Bn with XhoI, was then introduced into the SalI site of a vector pSKA-VAt (Kodama (2003)), in which AhRV and Arnt, to which a 5' untranslated (UTR) sequence of alfalfa mosaic virus was respectively added, were inserted in the forward direction into two sets of expression units consisting of a CamV35S promoter and an nos terminator in a binary vector pBin19, to construct pSBP1459.

pSPB1459 was then introduced into *Agrobacterium tumefaciens* strain Ag10 (BioTechnology, 9, 963-967 (1991)) to transform petunia (variety PL, Skr4 xSw63 (same as in Nature, 366, 276-279) according to the *Agrobacterium* method using a leaf disc. Introduction of plasmid into *Agrobacterium* and transformation were carried out in accordance with a known method (Plant J., 5, p. 81-82 (1994)). Although flower color of variety PL is white to light pink since it lacks flavonoid 3',5'-hydroxylase gene and flavonoid 3'-hydroxylase gene, the petunia variety used for the purpose of this experiment is not limited to PL. 38 independent strains of transformed petunia PAB were acquired.

(2) Example of Infection to Torenia—Part 1

Using torenia for the floricultural plant, a selectable marker gene in the form of GFP gene was introduced as a foreign gene.

CaMV35S-sGFP(S65T)-NOS3' (Curr. Biol., 6, 325-330 (1996)) was digested with BamHI and EcoRI, and DNA (1.0 kb) linking sGFP gene and nos terminator gene was introduced into the BamHI/EcoRI site of pBluescriptII (sk-) to construct a plasmid pB-Gn. A gene cassette consisting of GUS gene and nos terminator was excised from pBlueSXX-REGUS-last with XbaI and KpnI, and a gene cassette (1.0 kb) consisting of sGFP and nos terminator excised from pB-Gn with XbaI and KpnI was introduced into the same site to construct pB-X6Gn. A gene cassette (1.2 kb) consisting of 6xXRE promoter, sGFP and nos terminator excised from pB-X6Gn by digesting with XhoI was then introduced into the SalI site of pSKAVAt to construct pSPB1458.

pSPB1458 was then introduced into *Agrobacterium tumefaciens* strain Ag10 followed by transforming torenia (variety Summer Wave Blue: SWB (Suntory Flowers) to a leaf disc according to the *Agrobacterium* method using a leaf disc. Transformation of torenia was carried out in accordance with a known method (Mol. Breeding, 6, 239-246 (2000)). Although the flower color of the SWB variety is blue, the variety of torenia used for the purpose of this experiment is not limited to SWB. 40 independent strains of transformed torenia TAG were acquired.

(3) Example of Infection into Torenia—Part 2

Using torenia for the horticultural plant, a gene involved in flavonoid synthesis was introduced as a foreign gene.

A construct (pSFL307 or pSFL308), having an expression cassette of a gene involved in aurone synthesis and a cassette for inhibiting expression of anthocyanin synthesis-related genes by RNAi, was introduced using torenia variety Summer Wave Blue as the host plant according to a method using *Agrobacterium* in the same manner as described above. The flower color of the resulting torenia changed from blue to yellow.

(4) Example of Infection into Tobacco, Verbena or Nierembergia

Using tobacco, verbena or nierembergia for the floricultural plant, a transcription factor gene was introduced as a foreign gene.

Thale cress PHRI gene (Genes & Development, 15: 2122-2133(2001)), which is expressed under phosphate starvation conditions, was subcloned in a pCR2.1 vector using a TOPO-TA Cloning Kit (Invitrogen) in accordance with the manual. A product amplified by a PCR reaction using primers PHRf (5'-ATGGAGGCTCGTCCAGTTCAT-3' (SEQ ID NO: 16)) and PHRr (5'-TCAATTATCGATTTTGGGACGC-3' (SEQ ID NO: 17)) was subcloned and designated as pSPB 1892. A binary vector pSPB2311, having an (Mac) promoter linking an enhancer sequence of a 35 S promoter and a mannopine synthase promoter, and a mannopine synthase (mas) terminator, was excised with SmaI to obtain pSPB2311A. A fragment smoothened by excising pSBP1892 with EcoRI was then inserted into pSBP2311 A to obtain pSBP2314.

Continuing, *Agrobacterium* (strain Ag10) was then transformed using pSBP1898 based on a known method (Plant J., 5, 81, 1994), and tobacco, verbena and Nierembergia were transformed using the transformant *Agrobacterium* having pSPB1898. Transformation of tobacco, verbena and Nierembergia was respectively carried out based on known methods (Science, 227, 1229, 1985; Plant Cell Rep., 21, 459, 2003; and, Plant Biotech., 23, 19, 2006). Gene introduction in the resulting plant bodies was confirmed by extracting DNA from a leaf of each plant body followed by PCR using PHR1 gene as a template. 11 PHR1 transgenic plants were acquired from tobacco, 16 from verbena and 1 from Nierembergia.

(5) Example of Infection into Impatiens and Begonia

Using impatiens or begonia for the floricultural plant, a transcription factor gene was introduced as a foreign gene.

Transformation of impatiens (Impatiens walleriana) was basically carried out using the varieties Glitter Red (Sakata Seed) and Tempo Pink (Takii & Co.) in accordance with U.S. Pat. No. 6,121,511. After pre-culturing shoot apices, nodes, leaf stalks and leaf sections cut from an in vitro seedlings for 5 days in a preculturing liquid medium (MS medium containing 1 mg/L of TDZ), the samples were allowed to stand undisturbed for 48 hours in a preculturing solid medium (MS medium containing 0.05 mg/L of NAA, 6 mg/L of zeatin and 0.3% gellan gum). Subsequently, the samples were infected with *Agrobacterium* (strain Ag10) containing pSPB2314 followed by culturing for 4 to 8 weeks on a selective medium (MS medium containing 0.05 mg/L of NAA, 6 mg/L of zeatin, 100 mg/L of kanamycin, 500 mg/L of carbenicillin, 100 mg/L of cefotaxime and 3% gellan gum) to obtain shoots (Table 9). Shoots were unable to be obtained from the leaf sections since they browned easily. Although numerous shoots were obtained from a single explant in the case of shoot apices and nodes, these were thought to contain a large number of false positives. Expression took a considerable amount of time in shoots obtained from leaf stalks, and although they were few in number, they appeared to be the most reliable.

Transformation of begonia (Begonia semperflorens) was carried out using the varieties Ambassador White and Ambassador Scarlet (Sakata Seed). Leaf sections and leaf stalks were cut out from in vitro seedlings and infected with *Agrobacterium* (strain Ag10) containing pSPB2314, followed by culturing for 3 days in the dark on co-cultivation medium (MS medium containing 0.5 mg/L of IAA, 0.1 mg/L of TDZ, 0.5% PVP, 2 mg/L of $AgNO_3$, 200 µM acetosyringone and 0.3% gellan gum). Subsequently, the samples were cultured for 3 to 5 days in pre-selective medium (MS medium containing 1 mg/L of BAP, 1 mg/L of zeatin, 0.1 mg/L of IAA, 500 mg/L of timentin, 50 µM acetosyringone and 0.25% gellan gum), followed by consecutively culturing for 2 weeks in selective medium 1 (MS medium containing 2 mg/L TDZ, 0.1 mg/L NAA, 100 mg/L of kanamycin, 500 mg/L of timentin and 0.4% agar), culturing for 2 weeks in selective medium 2 (MS medium containing 0.2 mg/L of BAP, 0.1 mg/L of NAA, 100 mg/L of kanamycin, 500 mg/L of timentin and 0.4% agar), and 3 weeks in selective medium 3 (MS medium containing 100 mg/L kanamycin, 500 mg/L of timentin and 0.4% agar). Surrounding tissue was cut away from the shoots that formed during that time when they grew to a diameter of 5 mm or more, the shoots were transferred to a selective medium 4 (MS medium containing 150 mg/L of kanamycin, 500 mg/L of timentin and 0.4% agar), and after further culturing for 2 to 3 weeks, the shoots were transferred to root initiation medium (MS medium containing 100 mg/L of kanamycin, 500 mg/L of timentin and 0.4% agar) to obtain root forming shoots (Table 10).

TABLE 9

Numbers of *Impatiens* Shoots

| Variety | Explant Source | No. of Infected Explants | No. of Resulting Shoots |
|---|---|---|---|
| Glitter Red | Leaf | 30 | 0 |
| | Shoot apex | 82 | 187 |
| | Node | 145 | 89 |
| | Leaf stalk | 90 | 0 |
| Tempo Pink | Leaf | 35 | 0 |
| | Shoot apex | 196 | 333 |
| | Node | 418 | 184 |
| | Leaf stalk | 259 | 5 |

TABLE 10

Numbers of *Begonia* Shoots

| Variety | No. of Infected Explants | No. of Resulting Shoots |
|---|---|---|
| Ambassador White | 940 | 13 |
| Ambassador Scarlet | 805 | 2 |

As is indicated above, a foreign gene was determined to be able to be introduced using *Agrobacterium* in floricultural plants other than roses and carnations such as petunias, torenia, tobacco, verbena, nierembergia, impatiens or begonias. The introduced foreign gene is not limited to the specific genes exemplified here, but rather any gene is considered to be able to be introduced into these floricultural plants using similar methods provided it is a gene that functions in L1 cells following introduction. Since the technology of the present invention can be applied to floricultural plants into which a foreign gene can be introduced using *Agrobacterium*, with respect to these plants, it is possible to produce a floricultural plant of the present invention, namely a floricultural plant in which a foreign gene is only present in a part of the cells of the transgenic plant but not present in other cells.

INDUSTRIAL APPLICABILITY

A transgenic plant produced according to the method disclosed by the present invention is a chimeric plant that does not have an introduced gene in the L2 cell layer that includes germ cells and the like, but rather only has the introduced gene in cells of the L1 layer. Since this type of transformant does not have an introduced gene in germ cells, the possibility of the transgenic plant being freely used as a crossing parent by an unauthorized third party can be prevented.

In addition, since there is concern regarding transgenic plants over dispersal of an introduced gene into the natural world, the possibility of introduced gene dispersal can be completely negated by producing a transgenic plant does not have an introduced gene in the germ cells thereof. Accordingly, the burden placed on persons attempting to use a transgenic plant industrially with respect to application for approval for commercial use of a transgenic plant (in Japan, the "Law Concerning the Conservation and Sustainable Use of Biological Diversity through Regulations on the Use of Living Modified Organisms" (Cartagena protocol)) can be reduced.

The invention claimed is:

1. A rose that contains a foreign gene in cells of the L1 layer, but not in pollen cells and ovule cells, wherein the foreign gene is at least one of a flavonoid 3',5'-hydroxylase gene from a plant belonging to the violet family, and an aromatic acyl group transferase gene from a plant belonging to the snapdragon family.

2. The rose of claim 1, wherein the rose is Rosa hybrida.

3. The rose of claim 2, wherein the rose is a hybrid tea rose, a floribunda, or a miniature rose.

4. The rose of claim 1, wherein the flavonoid 3',5'-hydroxylase gene is from a pansy.

5. The rose of claim 1, wherein the aromatic acyl group transferase gene is from a torenia.

6. A method for producing the rose of claim 1, comprising introducing the foreign gene into the rose mediated by *Agrobacterium*, and selecting the rose in which the foreign gene is only present in cells of the L1 layer.

7. The rose of claim 1, wherein the flavonoid 3',5'-hydroxylase gene comprises the nucleic acid sequence of SEQ ID NO: 4.

8. The rose of claim 1, wherein the flavonoid 3',5'-hydroxylase gene encodes a flavonoid 3',5'-hydroxylase comprising the amino acid sequence of SEQ ID NO: 19.

9. The rose of claim 1, wherein the aromatic acyl group transferase gene comprises the nucleic acid sequence of SEQ ID NO: 3.

10. The rose of claim 1, wherein the aromatic acyl group transferase gene encodes an aromatic acyl group transferase comprising the amino acid sequence of SEQ ID NO: 18.

* * * * *